(12) United States Patent
Tabakoff

(10) Patent No.: US 10,391,088 B2
(45) Date of Patent: *Aug. 27, 2019

(54) ANALGESIC COMPOSITIONS

(71) Applicant: Lohocla Research Corporation, Evanston, IL (US)

(72) Inventor: Boris Tabakoff, Elizabeth, IL (US)

(73) Assignee: Lohocla Research Corporation, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/125,252

(22) Filed: Sep. 7, 2018

(65) Prior Publication Data

US 2019/0099412 A1    Apr. 4, 2019

Related U.S. Application Data

(63) Continuation-in-part of application No. 15/318,964, filed as application No. PCT/US2015/036473 on Jun. 18, 2015, now Pat. No. 10,112,905.

(60) Provisional application No. 62/015,152, filed on Jun. 20, 2014.

(51) Int. Cl.
*A61K 31/4706* (2006.01)
*A61K 31/616* (2006.01)
*A61P 25/04* (2006.01)
*A61K 31/137* (2006.01)
*A61K 31/485* (2006.01)
*A61K 31/196* (2006.01)

(52) U.S. Cl.
CPC ........ *A61K 31/4706* (2013.01); *A61K 31/137* (2013.01); *A61K 31/196* (2013.01); *A61K 31/485* (2013.01); *A61K 31/616* (2013.01); *A61P 25/04* (2018.01)

(58) Field of Classification Search
CPC .................. C07D 215/48; A61K 31/4706; A61K 31/485; A61K 31/616; A61K 31/137; A61K 31/196
See application file for complete search history.

(56) References Cited

U.S. PATENT DOCUMENTS 10,112,905 B2 * 10/2018 Tabakoff .............. C07D 215/46
2019/0092731 A1 *  3/2019 Tabakoff .............. C07D 215/48

OTHER PUBLICATIONS

Offord, The scientist Magazine, Jan. 2018, 2019, 1-9. (Year: 2018).*

* cited by examiner

*Primary Examiner* — D Margaret M Seaman
(74) *Attorney, Agent, or Firm* — Olson & Cepuritis, Ltd.

(57) ABSTRACT

Analgesic compositions comprise an aminoquinoline together with an opioid, a non-steroidal anti-inflammatory drug (NSAID), a NE/5-HT reuptake inhibitor, or a combination thereof. The aminoquinoline potentiates bioactivity of opioids, NSAIDs and NE/5-HT reuptake inhibitors.

46 Claims, 19 Drawing Sheets

Fig. 1 Blood DCUKA Level After Oral Administration of 50 or 100mg/kg DCUK-OEt in HPMCAS-MG SDD Fig. 3 Effect of DCUKA, BCUKA and Gabapentin on Cisplatin-Induced Neuropathic Pain Fig. 4  Effect of DCUKA on CFA-induced neuropathic pain

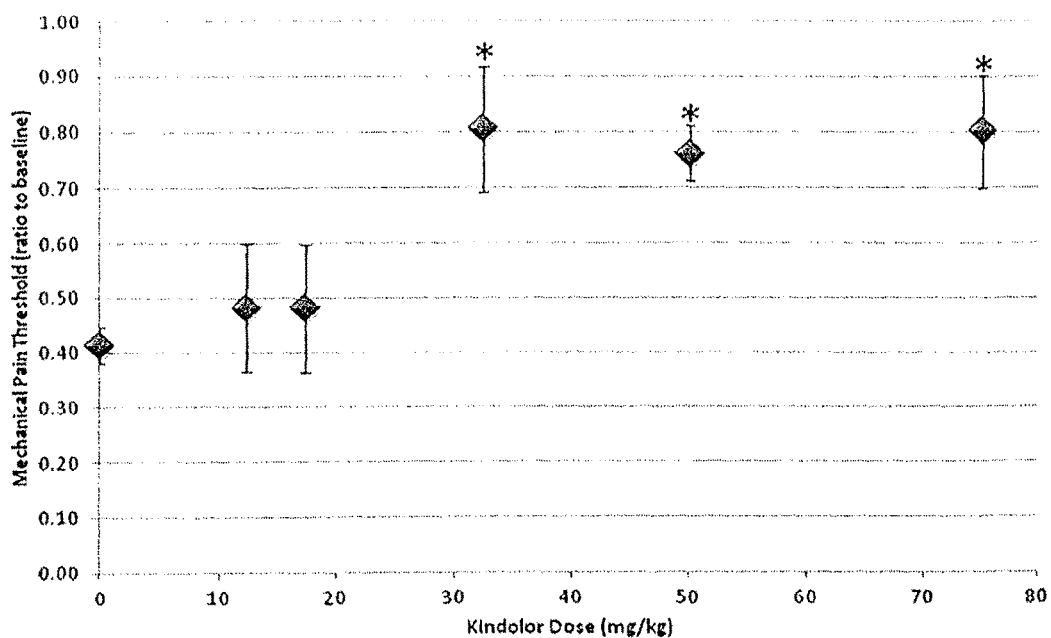

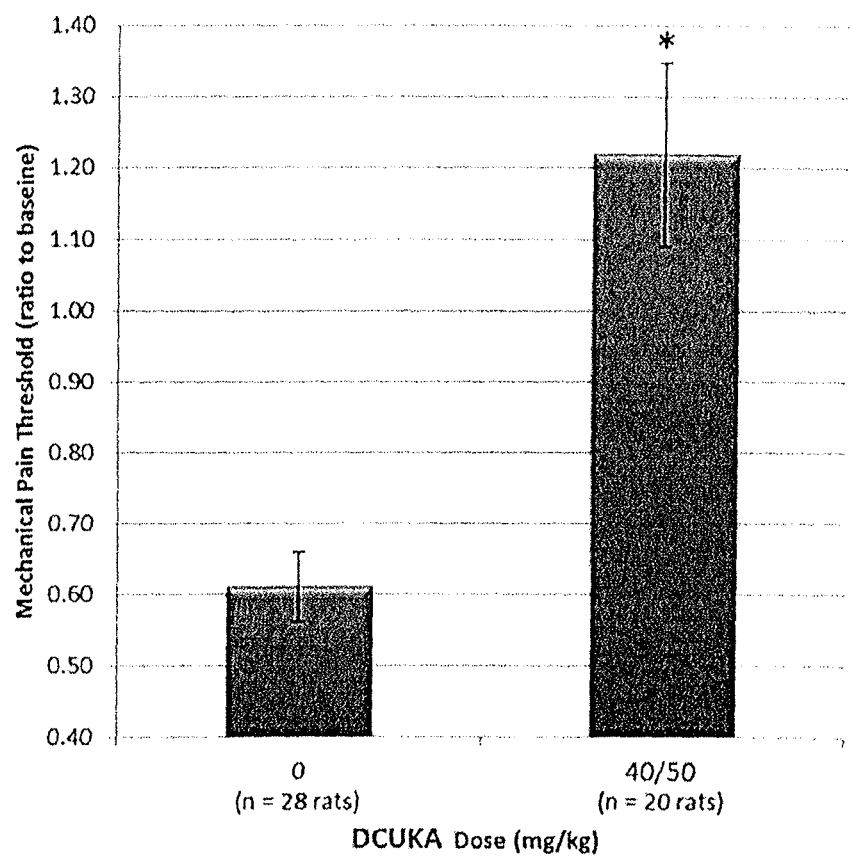

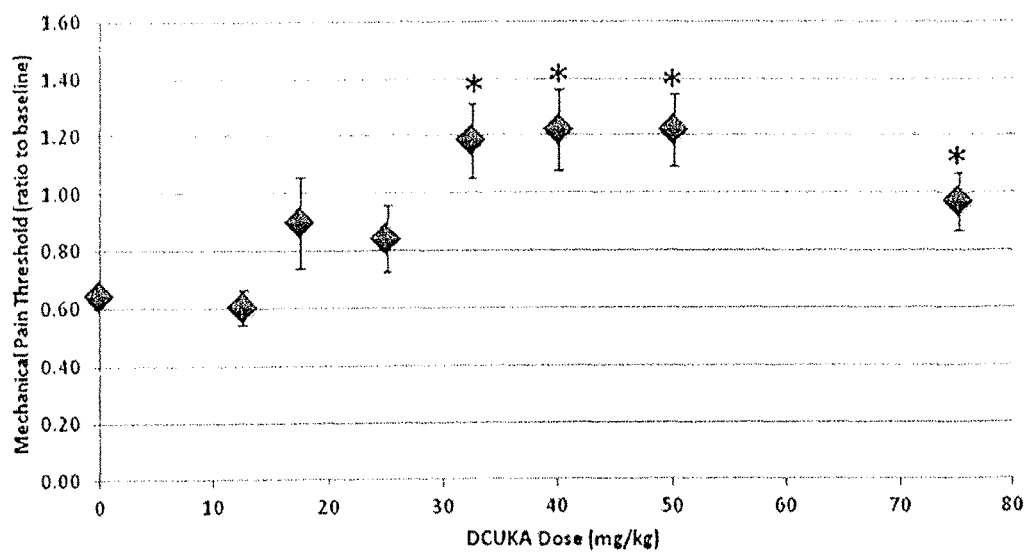

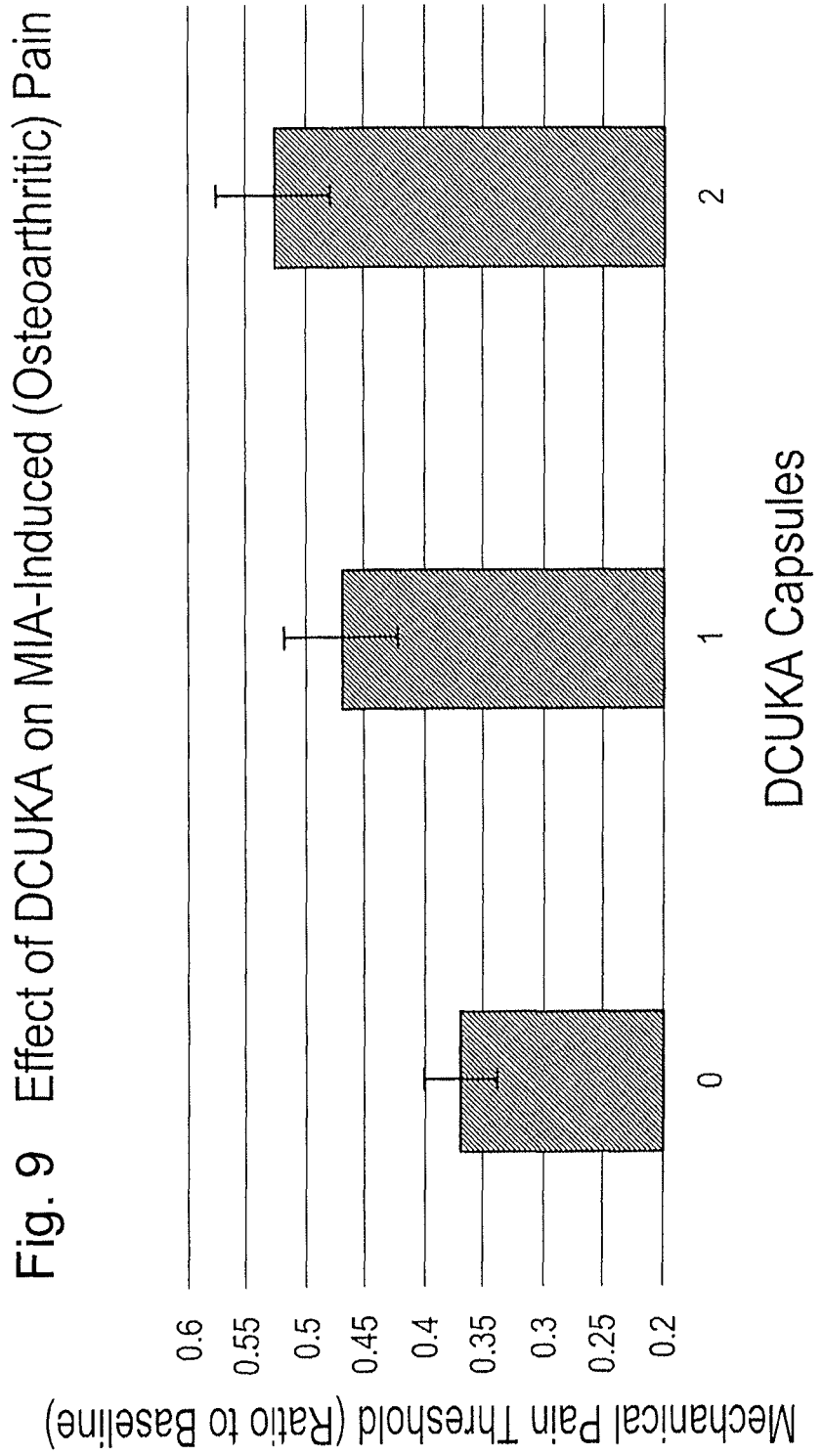
Fig. 9 Effect of DCUKA on MIA-Induced (Osteoarthritic) Pain

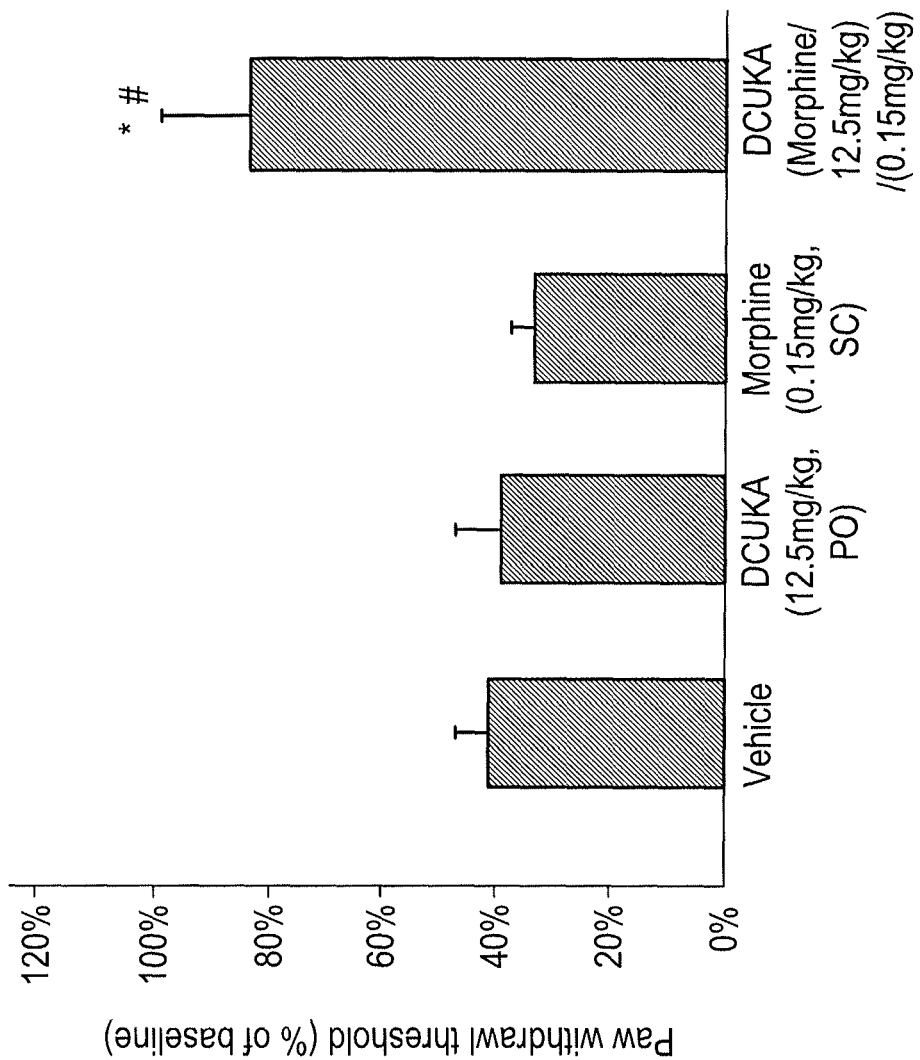

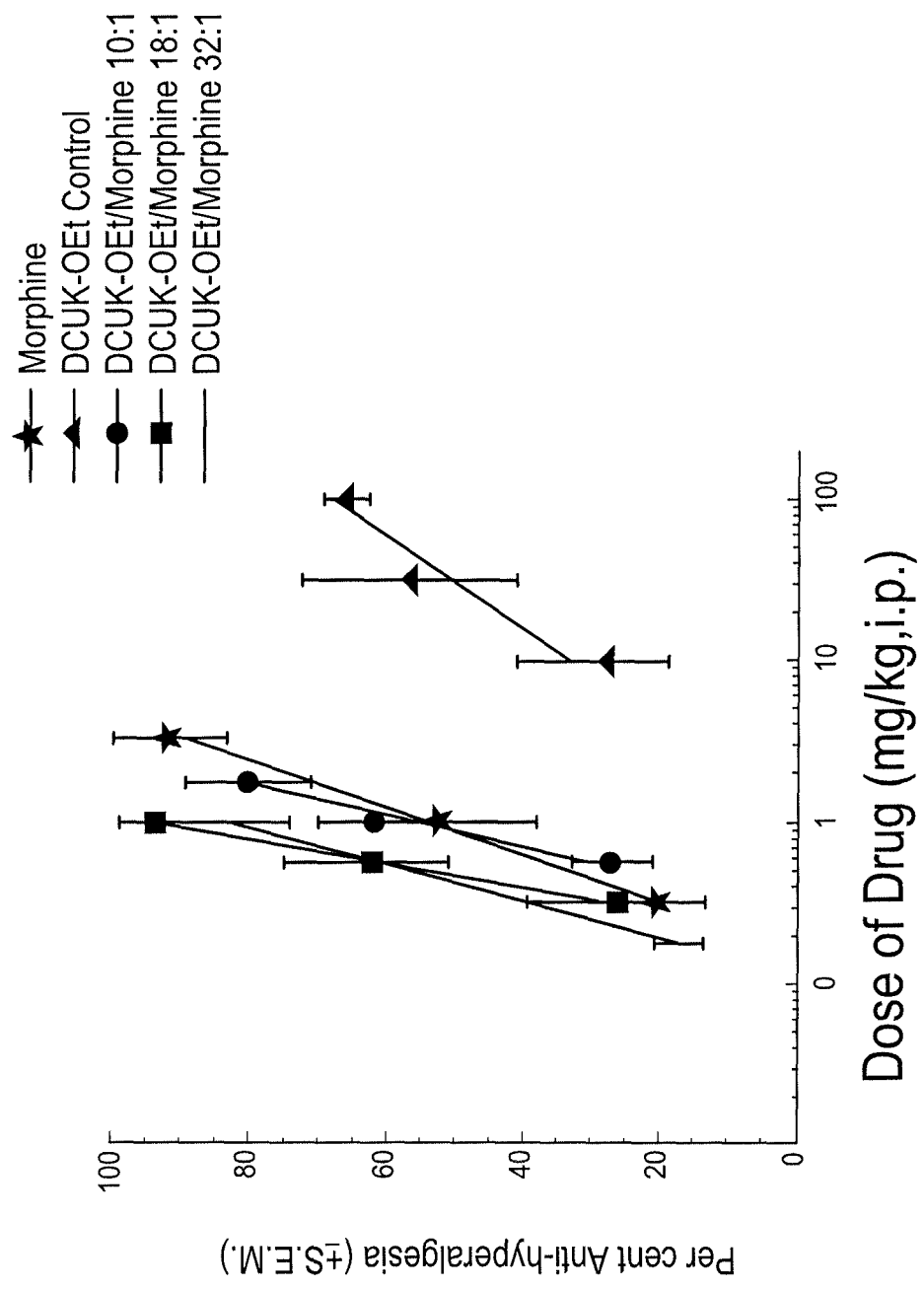
Fig. 10B Interactions on Thermal Anti-hyperalgesia in CFA Model

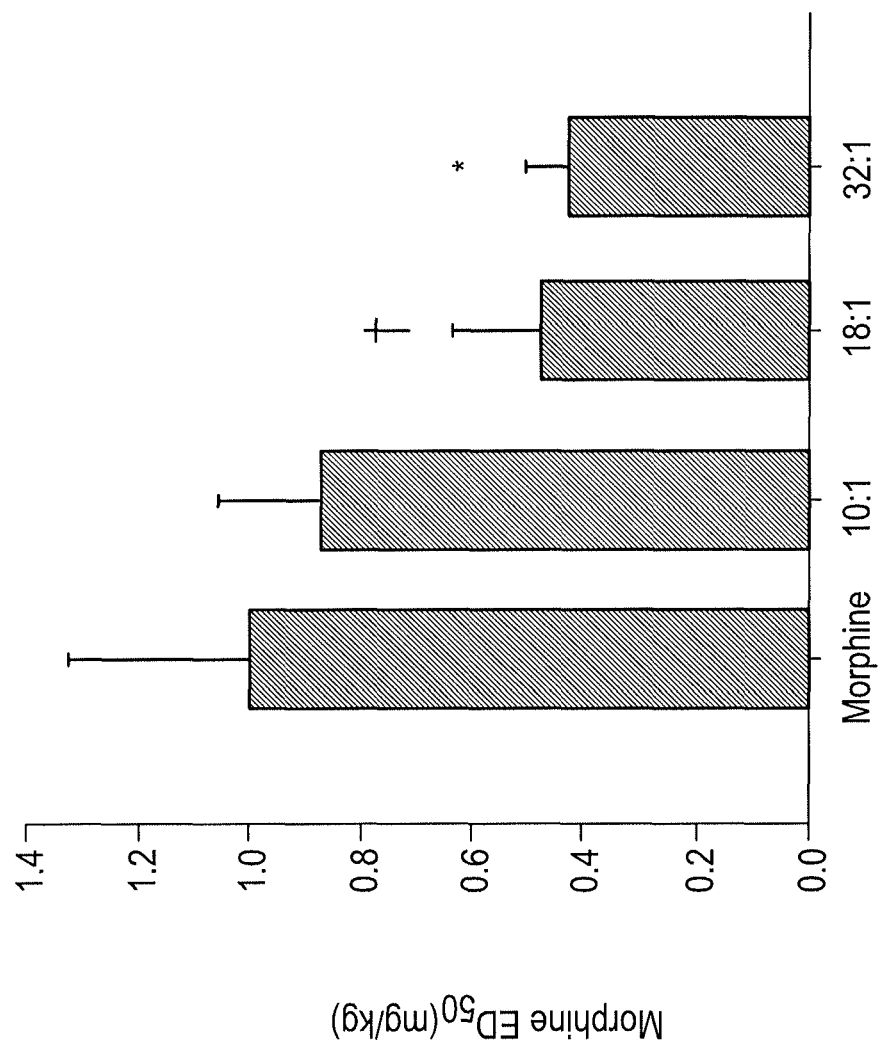

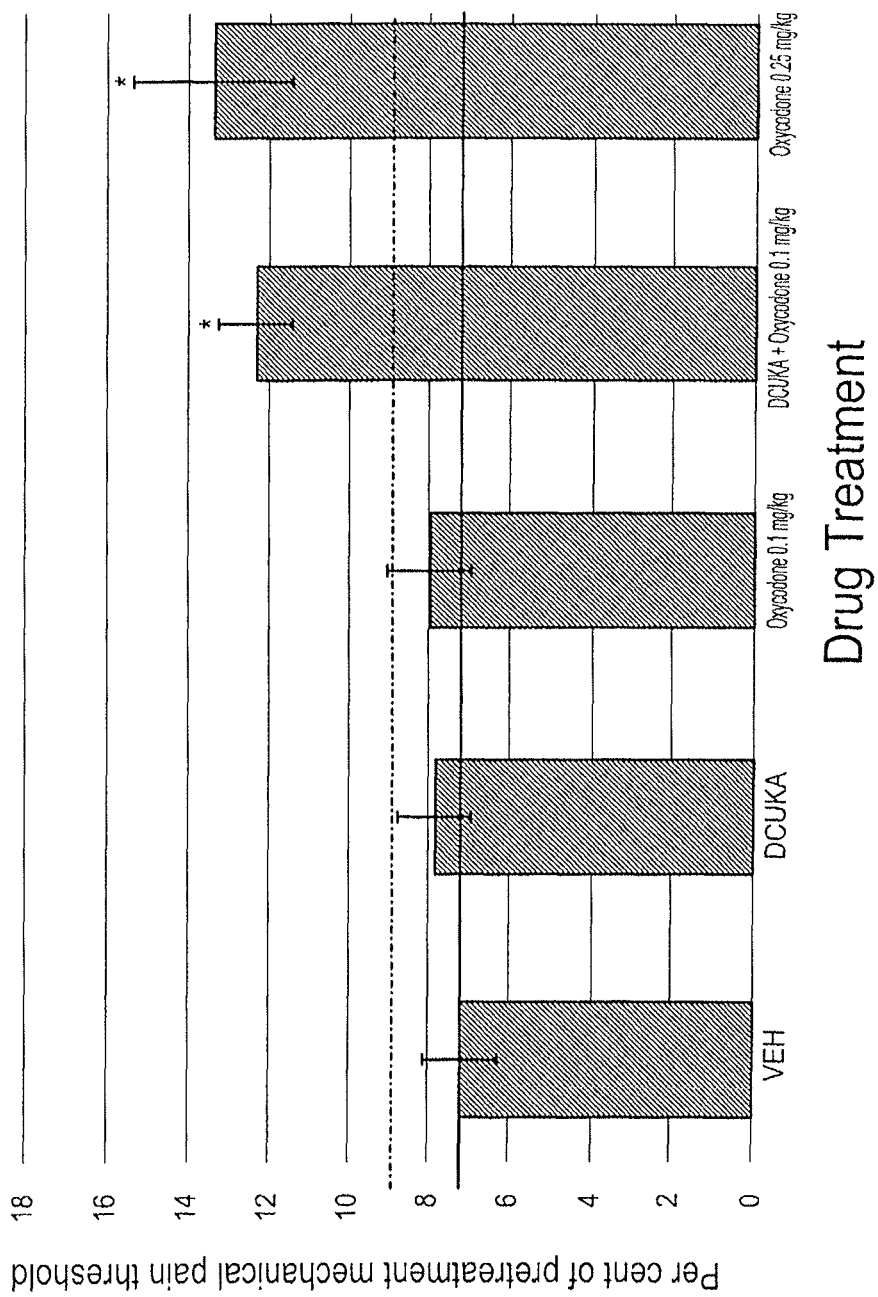

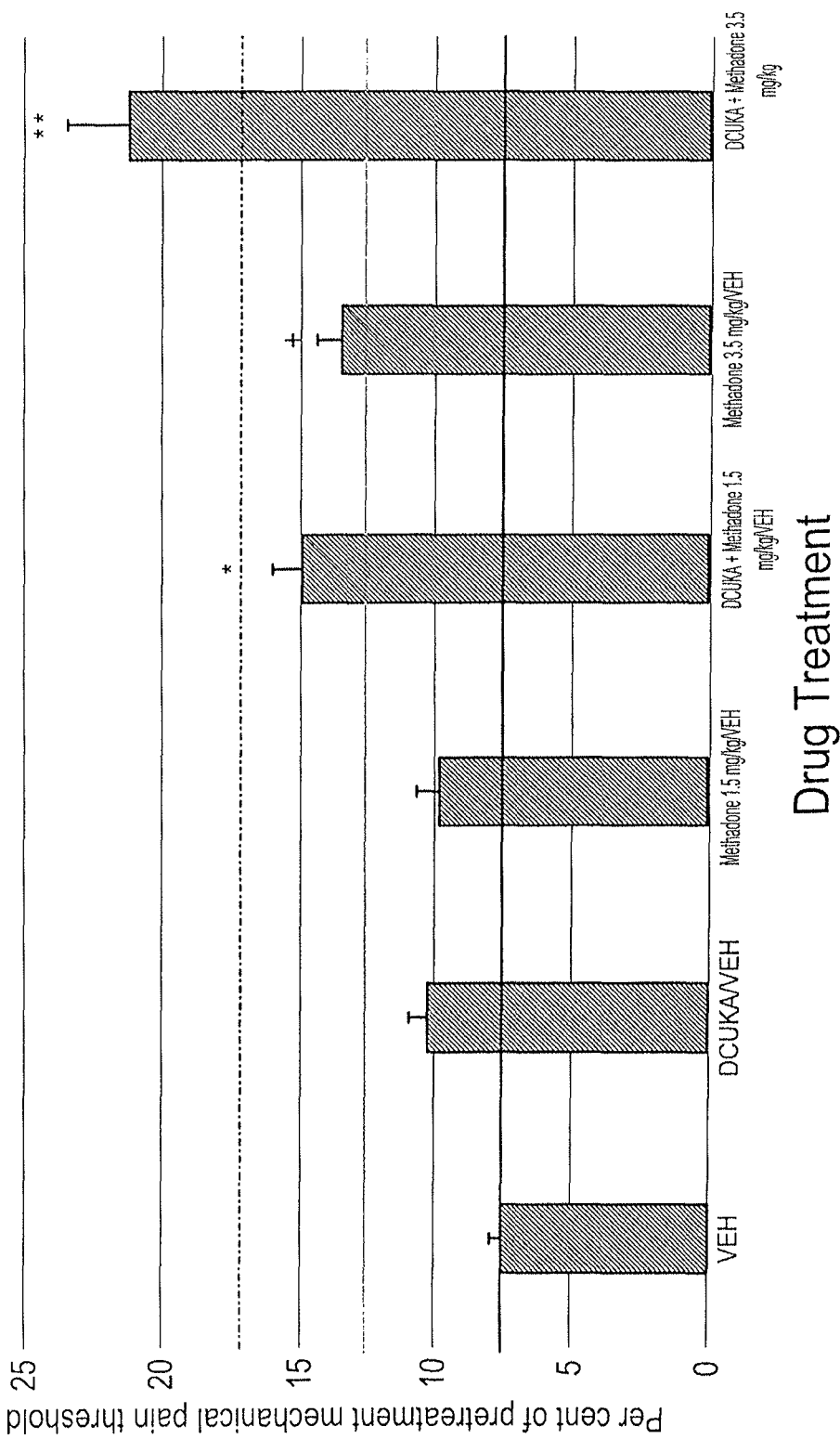
Fig. 12 Effect of DCUKA plus Methadone on FA-Induced Pain

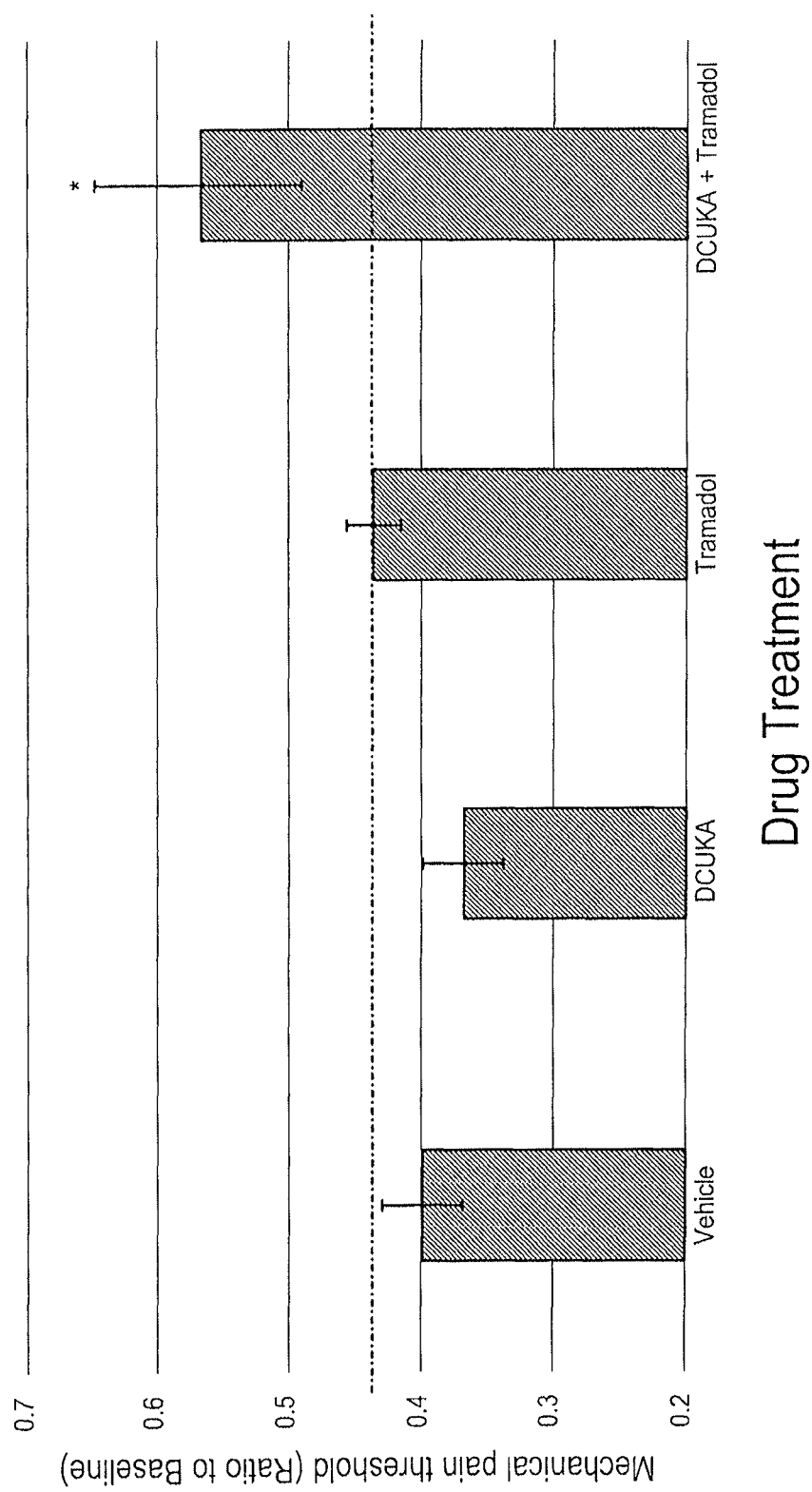
Fig. 13 Effect of DCUKA plus Tramadol in Combination on MIA-Induced Pain Fig. 15 Effect of DCUKA plus Diclofenac on FA-Induced Pain DCUKA prevention of the development of CFA induced inflammatory pain

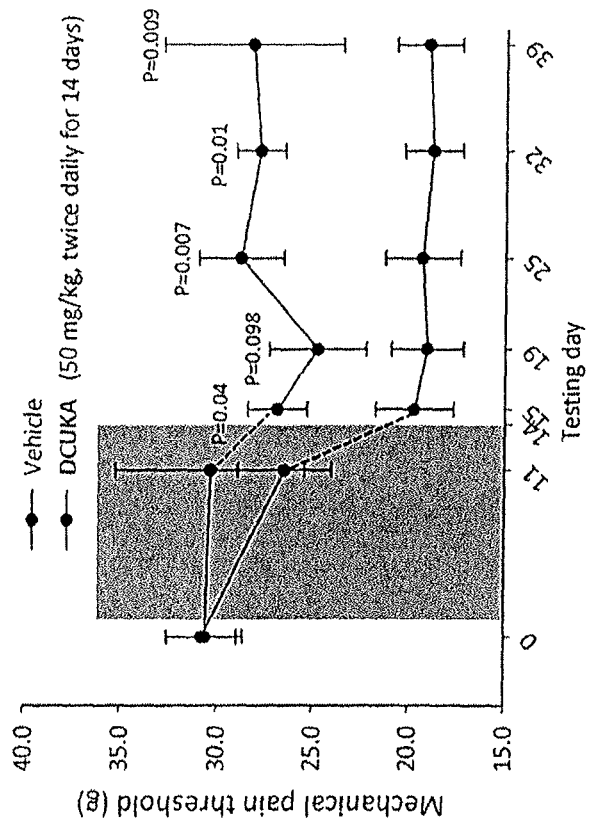
Fig. 17 DCUKA prevents the development of cisplatin-induced neuropathic pain

ANALGESIC COMPOSITIONS

CROSS-REFERENCE TO RELATED APPLICATIONS

This application is a continuation-in-part of U.S. patent application Ser. No. 15/318,964, filed on Dec. 14, 2016, which application is a National Phase entry of PCT/US2015/036473, filed on Jun. 18, 2015, and claims benefit of U.S. Provisional Application Ser. No. 62/015,152, filed on Jun. 20, 2014, all incorporated herein by reference in their entireties.

GOVERNMENT SUPPORT

This invention was made with government support from the National Institutes of Health, Grant No. R44-AA-009930. The United States government has certain rights in this invention.

FIELD OF THE INVENTION

The present invention relates to analgesic compositions containing aminoquinoline compounds together with opioids, norepinephrine/serotonin reuptake inhibitors and/or non-steroidal anti-inflammatory drugs (NSAIDs)

BACKGROUND OF THE INVENTION

Although acute pain in response to injury is an important mechanism for reducing the extent of harm to an individual, the nervous system can undergo an adaptive change that results in pain that is perceived well beyond the time after the injury is healed (chronic pain) (Costigan et al., 2009). This chronic pain can be generated by a stimulus that is normally innocuous (allodynia), or the response to a noxious stimulus can be greatly exaggerated (hyperalgesia). Chronic pain is estimated to affect at least 100 million adults in the United States and can negatively affect quality of life (Institute of Medicine, 2011). The pharmacologic treatment of neuropathic (due to nerve injury) or other chronic pain relies heavily on the use of opiates or their derivatives (Reuben et al., 2015). These drugs have many adverse effects, including tolerance/hyperalgesia, which results in dose escalation, and the development of opiate addiction (Chou et al., 2015). Additional side effects of high dose, chronic administration of opiates include constipation, sleep-disordered breathing, fractures, hypothalamic-pituitary-adrenal dysregulation, and overdose, as well as effects on the cardiovascular and immune systems (Baldini et al., 2012). Other drugs, including non-steroidal anti-inflammatory drugs (NSAIDs), anticonvulsants, muscle relaxants and antidepressants, as well as drugs targeting voltage-sensitive calcium channels (gabapentin and pregabalin) are used to treat chronic pain, but these treatments provide limited relief (Lunn et al., 2014; Moore et al., 2014; Schreiber et al., 2015; Smith et al., 2012; Sofat et al., 2017; Lozada, et al., 2008). In addition, chronic administration of high doses of NSAIDs, the next most popular drugs, after opioids, for treatment of chronic pain, is associated with a plethora of side effects, including stomach problems (such as bleeding, ulcer, and stomach upset), renal failure, high blood pressure or cardiac problems, fluid retention, rashes, or other allergic reactions (Marcum and Hanlon 2010). A third category of drugs to treat chronic pain are the more recently introduced blockers of the 5-HT and NE reuptake systems (Smith et al., 2012; Sofat et al., 2017). 5-HT/NE reuptake inhibitors also present a series of side effects including nausea, G.I. disturbances, fatigue but difficulty sleeping. More dangerous are the effects of rapidly stopping the use of these drugs if they are not relieving the chronic pain. These "withdrawal" effects include extreme mood swings, agitation, aggression, nightmares, confusion and electric shock-like sensations in the head and other parts of the body (Fava et al., 2018; Carvalho et al., 2016). In all cases, be it with opiates/opioids, NSAIDs or 5-HT/NE reuptake inhibitors, the escalation of dose for therapeutic success against chronic pain results in the emergence of severe side effects and more severe withdrawal signs if the use of the medication is stopped abruptly.

The majority of chronic pain sufferers, whose pain is not controlled by other classes of drugs, continue to use prescribed opiates/opioids for prolonged periods and at high doses. Because of growing concerns about the significant increase in the use of opiates to treat chronic pain, and the accompanying problems of overdose, misuse and diversion, labeled the "opioid crisis", recommendations have been made to limit prescribed opioids to the lowest effective dose, and for the shortest effective duration, and importantly to develop new non-opioid medications based on scientific information about the etiology of chronic pain (Volkow and McLellan 2016; Taneja et al., 2017; Kirkpatrick et al., 2016).

Numerous attempts have been made to generate new and better pain medications by focusing on targets that are known to be involved in chronic pain (Yekkirala, et al., 2017; Worley 2017). Target selection is a key feature of chronic pain drug development efforts, and most programs have used the approach of targeting a single target/site, such as a receptor, which has been the approach of choice of the pharmaceutical industry for many years (Ramsay et al., 2018). However, targeting a single molecular entity to control a complex physiological system has resulted in agents with limited efficacy (Bozic et al., 2013). More recently, perceptions have changed, in part due to the design of effective multi-target drugs for treatment of schizophrenia, viral infections, asthma, cardiovascular disease, neurodegenerative disease and cancer (Ramsay et al., 2018). Such drugs produce partial inhibition of more than one target within a network, rather than total inhibition of a single target (Zimmerman et al., 2007; Millan, 2014; Talevi, 2015).

With regard to pain, one can focus on the systems that conduct sensory information from peripheral receptors, and those that transduce information within and between sensory neurons. One of the most investigated molecular mechanisms leading to chronic neuropathic pain syndromes is an upregulation of the activity of peripheral voltage-sensitive sodium channels (VSNaCs) (Wood et al., 2004; Lai, et al., 2004; Black et al., 2004; Coggeshall et al., 2004; Dib-Hajj et al., 2007). The tetrodotoxin-sensitive Nav1.7 channel is located along the projections and cell bodies of the slowly conducting nociceptive neurons, and its role in both acute and chronic pain has been clearly demonstrated by genetic manipulation in animals and by naturally-occurring genetic mutations in humans (Black et al., 2004; Wang et al., 2011; Lawrence, 2012). The Nav1.7 channel has been particularly linked to pain associated with inflammation, and its upregulation contributes to the increased generation and conduction of action potentials in chronic pain syndromes (Eijkelkamp et al., 2012). In addition, the activity of the Nav1.7 channel can amplify generator potentials and promote the activation of other sensory neuron VSNaCs including the tetrodotoxin-resistant Nav1.8 channel (Dib-Hajj et al., 2007; Choi & Waxman, 2011). The Nav1.8 channel has been linked to development of both inflammatory and neuropathic pain conditions. Overall, the upregulation of the activity of the Nav1.7 and Nav1.8 channels in peripheral sensory neurons constitutes a common component of induction and maintenance of chronic pain syndromes (Wang et al., 2011; Theile & Cummins, 2011; Laedermann et al., 2015).

The role of the excitatory amino acid, glutamate, in the physiology of normal pain sensing and transmission of chronic pain phenomena is also well established (Davies & Lodge, 1987; Dickenson & Sullivan, 1987; Childers & Baudy, 2007). Sensory neuron activation or damage produces increased release of glutamate from both peripheral and central neurons, and the released glutamate can act on nearby glutamate (NMDA) receptors, to contribute to peripheral sensitization (Fernandez-Montoya et al., 2017; Jang et al., 2004). The interaction of glutamate with NMDA receptors in the dorsal root ganglia (DRG) is also involved in amplification of sensory signals (Ferrari et al., 2014; Rozanski et al., 2013). NMDA receptors are therefore involved in both the initiation and amplification of a pain sensation and its transmission into the CNS. Upregulation of NMDA receptors is seen both in peripheral neurons and spinal cord after sensory nerve damage, and this upregulation is thought to contribute to chronic neuropathic pain (Petrenko et al., 2003). In particular, the quantity of the GluN2B (NR2B) subunit-containing NMDA receptors plays the most important role in development and maintenance of chronic pain syndromes (Karlsson et al., 2002; Iwata et al., 2007; Gaunitz et al., 2002; Wilson et al., 2005).

Based on this discussion, a medication that can simultaneously inhibit Nav1.7 and Nav1.8 channel activity, as well as inhibit the activity of NMDA receptors (particularly those that contain the GluN2B subunit), can be of benefit both in preventing the development of chronic pain by inhibiting receptor/channel upregulation, and in reducing pain even after the development of a chronic pain syndrome. Such a medication would not have to act in the central nervous system, but could prevent peripheral sensitization that leads to the development central sensitization and chronic pain, and/or dampen the initiation and transmission of chronic pain signals to the brain.

SUMMARY OF THE INVENTION

N-substituted-4-ureido-5,7-dichloro-2-carboxy (or carboxyester) quinolines in combination with opioids, NE/5-HT reuptake inhibitors or NSAIDs are effective in treatment and prevention of chronic neuropathic pain in humans.

Analgesic compositions embodying the present invention contain an aminoquinoline compound together with an opioid, a NE/5-HT reuptake inhibitor, a non-steroidal anti-inflammatory drug (NSAID), or a combination thereof. The aminoquinoline compound potentiates bioactivity of opioids, agents that block the uptake of serotonin (5-HT) and norepinephrine (NE), and NSAIDs. As a result, co-administration of the aminoquinoline compound allows for a lower dose of the opioid, NE or 5HT reuptake blocker, or NSAID to be used for a desired analgesic (antihyperalgesic) effect. In addition, the aminoquinoline compound, when administered early in the course of development of chronic pain, can present the development of chronic pain and/or exacerbation of chronic pain syndrome.

In the aminoquinoline compounds represented by Formula (I):

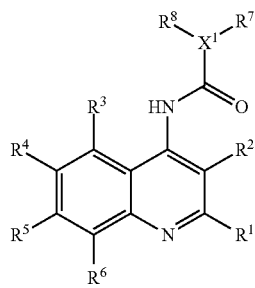

(I)

the substituents thereof are defined as follows: $R^1$ is H, $C_2$-$C_4$ alkyl, $C_2$-$C_4$ alkenyl, halo, $Z^1R^9$, or $N(R^{10})(R^{11})$. $R^2$ is H, $C_1$-$C_4$ alkyl, $C_2$-$C_4$ alkenyl, halo, $Z^2R^{12}$, $N(R^{13})(R^{14})$, or $C_1$-$C_4$ alkyl substituted with one or more moiety selected from the group consisting of $C_1$-$C_4$ alkyl, $C_2$-$C_4$ alkenyl, halo, $Z^3R^{15}$, $N(R^{16})(R^{17})$; each $R^3$, $R^4$, $R^5$, and $R^6$ independently is H, $C_1$-$C_4$ alkyl, $C_2$-$C_4$ alkenyl, halo, $Z^3R^{18}$, or $N(R^{19})(R^{20})$; $X^1$ is N or CH; each $R^7$ and $R^8$ independently is H, $C_1$-$C_6$ alkyl, $C_2$-$C_4$ alkenyl, $C_2$-$C_4$ alkynyl, aryl, or $C_1$-$C_6$ alkyl substituted with one or more moiety selected from the group consisting of $C_1$-$C_4$ alkyl, $C_2$-$C_4$ alkenyl, nitro, halo, $Z^4R^{21}$, and $N(R^{22})(R^{23})$; or $R^7$ and $R^8$ together with $X^1$ form a 5 to 8 member saturated, unsaturated, or aromatic organic cyclic or heterocyclic moiety; each $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ independently is H, $C_1$-$C_4$ alkyl, or $C_1$-$C_4$ alkyl substituted with one or more moiety selected from the group consisting of $C_1$-$C_4$ alkyl, $C_2$-$C_4$ alkenyl, $C_2$-$C_4$ alkynyl, halo, heteroaryl, $Z^5R^{24}$, and $N(R^{25})(R^{26})$. Each of $Z^1$, $Z^2$, $Z^3$, $Z^4$, and $Z^5$ independently is O, S, NH, C(=O)O, O—C (=O), C(=O), or C(=O)NH. Each $R^{24}$, $R^{25}$, and $R^{26}$ independently is $C_1$-$C_4$ alkyl with the proviso that when $R^1$ is $Z^1R^9$, $Z^1$ is C(=O)O, $R^9$ is H or $C_1$-$C_2$ alkyl, each of $R^3$ and $R^5$ is halo, $X^1$ is N, and each of $R^4$ and $R^6$ is H, then at least one of $R^7$ and $R^8$ is not a phenyl, alkoxy-substituted phenyl, or $C_1$-$C_6$ alkyl group.

In the aminoquinoline compounds of Formula (II):

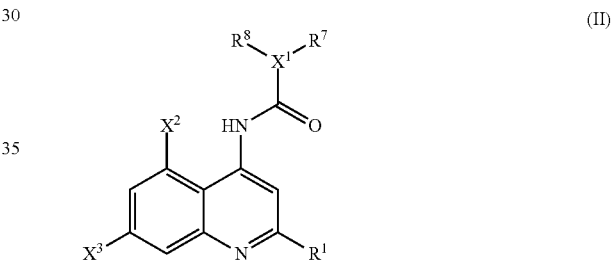

(II)

$X^1$, $R^1$, $R^7$ and $R^8$ are as defined in Formula (I) above, and each $X^2$ and $X^3$ independently is an electron withdrawing group such as halo, nitro, and the like, with the proviso that when $R^1$ is $Z^1R^9$, $Z^1$ is C(=O)O or C(=O), $R^9$ is H or $C_1$-$C_4$ alkyl, and $X^1$ is N, then at least one of $R^7$ and $R^8$ is not a phenyl or alkoxy-substituted group.

In the aminoquinoline compounds of Formula (III):

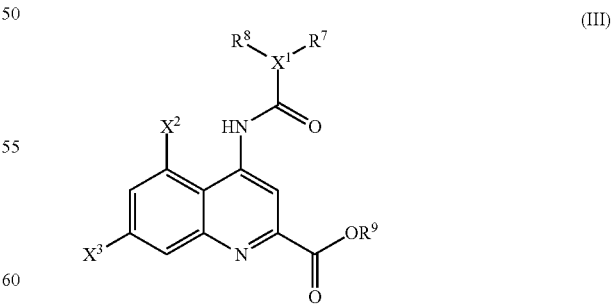

(III)

$X^2$ and $X^3$ each independently is halo, and each of $X^1$, $R^1$, $R^7$, $R^8$ and $R^9$ are as defined in Formulas (I) and (II) described above, with the proviso that when $R^9$ is H or $C_1$-$C_2$ alkyl, and $X^1$ is N, then at least one of $R^7$ and $R^8$ is not a phenyl or alkoxy-substituted phenyl group.

In the aminoquinoline compounds of Formula (IV):

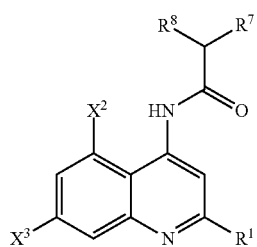

(IV)

each of $X^2$, $X^3$, $R^1$, $R^7$, and $R^8$ are as defined in Formulas (I) and (II) above.

In the aminoquinoline compounds of Formula (V):

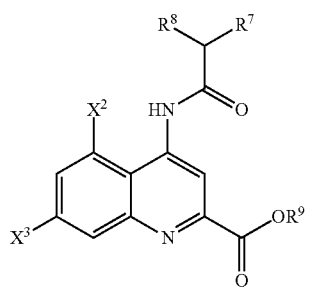

(V)

each of $X^2$, $X^3$, $R^7$, $R^8$ and $R^9$ are as defined in Formulas (I) and (II) above.

In the aminoquinoline compounds of Formula (VI):

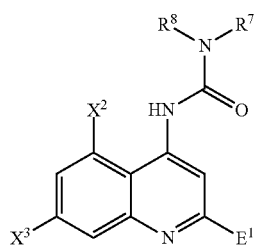

(VI)

$R^7$ is alkyl, cycloalkyl, aminoalkyl or phenyl; $R^8$ is H, alkyl, cycloalkyl, aminoalkyl, or phenyl; $E^1$ is —C(=O)$R^9$, —C(=O)$R^9$, —C(=O)N($R^9$)$_2$, and —[C($R^9$)$_2$]$_n$—O$R^9$; "n" is 1, 2, 3, or 4; each $R^9$ independently is H, $C_1$-$C_4$ alkyl, or $C_1$-$C_4$ alkyl substituted with one or more moiety selected from the group consisting of $C_1$-$C_4$ alkyl, $C_2$-$C_4$ alkenyl, $C_2$-$C_4$ alkynyl, halo, heteroaryl, $Z^5R^{24}$, and N($R^{25}$)($R^{26}$); $Z^5$ is O, S, C(=O)O or O—C(=O); each $R^{24}$, $R^{25}$, and $R^{26}$ independently is $C_1$-$C_4$ alkyl the alkyl; each $X^2$ and $X^3$ independently is an electron withdrawing group (preferably halogen or nitro); the alkyl, cycloalkyl, amino alkyl, and phenyl groups can be unsubstituted or substituted one or more times with an alkyl (1-3 carbons) group or an alkyloxy group (e.g., a 1 to 3 carbon alkyl or alkoxy group); and when acidic or basic functional groups are present, the compound can be in the free acid form, free base form, or can be a pharmacologically acceptable addition salt. When $E^1$ is C(=O)O$R^9$, at least one of $R^7$ and $R^8$ is not phenyl.

Particularly preferred for use in the present analgesic compositions are compounds of Formula (VI) in free acid form, free base form, or as a pharmacologically acceptable addition salt wherein:
$R^7$ is alkyl (preferably a 3 to 6 carbon alkyl), or phenyl;
$R^8$ is alkyl (preferably a 3 to 6 carbon alkyl), or phenyl;
$E^1$ is —C(=O)$R^9$;
each $R^9$ is H or $C_1$-$C_4$ alkyl; and
each $X^2$ and $X^3$ independently is an electron withdrawing group (preferably halogen or nitro).

Administration of the analgesic compositions can be by oral, subcutaneous, intravenous, intramuscular, intraperitoneal, transdermal or buccal routes.

Non-limiting examples of compounds of the general Formula (VI) are derivatives of the 2-carboxy-quinolines, e.g., (N, N-dibutyl)-4-ureido-5,7-dichloro-2-carboxy-quinoline (BCUKA), (N,N-diphenyl)-4-ureido-5,7-dichloro-2-carboxy-quinoline (DCUKA), and the like.

The di-substituted-4-ureido-5,7-dichloro-2-carboxy-quinoline compounds of Formula (VI) possess affinity for some or all of the following: Nav1.7, Nav1.8, and NMDA receptors. These compounds possess beneficial activity in treating chronic pain syndromes arising from degenerative joint pain (e.g., osteoarthritis) and inflammatory and mechanical damage to peripheral nerves, effectively ameliorating mechanical or thermal allodynia/hyperalgesia.

Compounds of Formula (VI) can be prepared by amidation of a 5,7-dichloroquinolone-2-carboxylate intermediate (e.g., obtainable by Michael addition of 3,5-dichloroaniline to dimethyl acetylene dicarboxylate, followed by thermal cyclization of the resultant aryl maleate) with chlorosulfonyl isocyanate to generate (4-amino)-5,7-dichloro-2-carboxy-quinoline ethyl ester (a key intermediate), which can be functionalized through reactions with relevant electrophiles. For preparation of monosubstituted ureas, a reactive urea intermediate is prepared through the reaction of a primary amine with carbonyldiimidazole. Reacting the resulting imidazoleurea with the amino-5,7-dichloro-2-carboxy-quinoline ethyl ester in the presence of sodium hydroxide yields a target monosubstituted urea at the 4 position of the quinoline, with concomitant ester hydrolysis. Removal of a protecting group, such as a tert-butoxycarbonyl (BOC)-protecting group, if such is used in the synthesis of the reactive urea intermediate, can be achieved with trifluoroacetic acid (TFA), to produce a desired TFA salt.

For preparation of disubstituted urea derivatives, the (4-amino)-5,7-dichloro-2-carboxy-quinoline methyl or ethyl ester is acetylated at the 4-amino position with a disubstituted carbamoyl chloride to form a (N, N-disubstituted)-4-ureido-5,7-dichloro-2-carboxy-quinoline ester. Optionally, the (N, N-di substituted)-4-ureido-5,7-dichloro-2-carboxy-quinoline-ester can be hydrolyzed to an (N, N-disubstituted)-4-ureido-5,7-dichloro-2-carboxy-quinoline.

DCUKA and DCUK-OEt each exhibit affinity for Nav1.7 and Nav1.8, and DCUKA also exhibits affinity for the NMDA receptor. DCUK-OEt can also act as a pro-drug for DCUKA, with ester hydrolysis by carboxylesterase 1 occurring after in vivo administration.

BRIEF DESCRIPTION OF THE DRAWINGS

FIG. 6 shows the results of a meta analysis of experiments to determine the dose dependent effect of DCUKA to reverse CFA-induced neuropathic pain.

FIG. 7 graphically illustrates the treatment by DCUKA (50 mg/kg) of pain caused by diabetic neuropathy. Rats were treated with streptozotocin (STZ) to induce diabetes, which reduced the mechanical pain threshold in comparison to baseline (pre-STZ treatment). DCUKA treatment reversed the mechanical pain threshold to baseline. The data show the ratio of the mechanical pain threshold after STZ or STZ plus DCUKA treatment to the pre-STZ mechanical pain threshold.

FIG. 8 shows the results of a meta-analysis of experiments to determine the dose-dependent effect of DCUKA to reverse STZ-induced neuropathic pain.

FIG. 9 graphically illustrates the treatment by DCUKA of osteoarthritic pain. Rats were treated with monoiodoacetic acid (MIA), which initiates an inflammatory reaction. Cartilage damage and degradation leads to chronic neuropathic pain, which is reflected in the lower mechanical pain threshold in comparison to baseline, measured in animals that received no MIA or drug. DCUKA reversed the mechanical pain threshold in a dose-dependent manner. The data show the ratio of the mechanical pain threshold after MIA or MIA plus DCUKA treatment to the mechanical pain threshold in animals that received no MIA or drug.

FIG. 10A shows graphically that administration of DCUKA enhances the ability of morphine to reverse CFA-induced neuropathic pain.

FIG. 10B shows graphically that administration of DCUK-OEt enhances the ability of morphine to reverse CFA-induced neuropathic pain.

FIG. 10C shows results of isobolographic analysis that demonstrates that DCUK-OEt significantly decreased the half-maximal effective dose of morphine needed to reverse pain.

FIG. 11 illustrates that DCUKA potentiates the ability of oxycodone to reverse CFA-induced neuropathic pain.

FIG. 12 illustrates that DCUKA potentiates the ability of methadone to reverse CFA-induced neuropathic pain.

FIG. 13 illustrates that DCUKA potentiates the ability of tramadol to reverse MIA-induced osteoarthritic (neuropathic) pain.

FIG. 17 illustrates graphically that administration of DCUKA simultaneously with the cancer chemotherapy agent cisplatin prevents the development of cisplatin-induced neuropathic pain, measured by changes in the mechanical pain threshold.

DETAILED DESCRIPTION OF PREFERRED EMBODIMENTS

Figure 1:
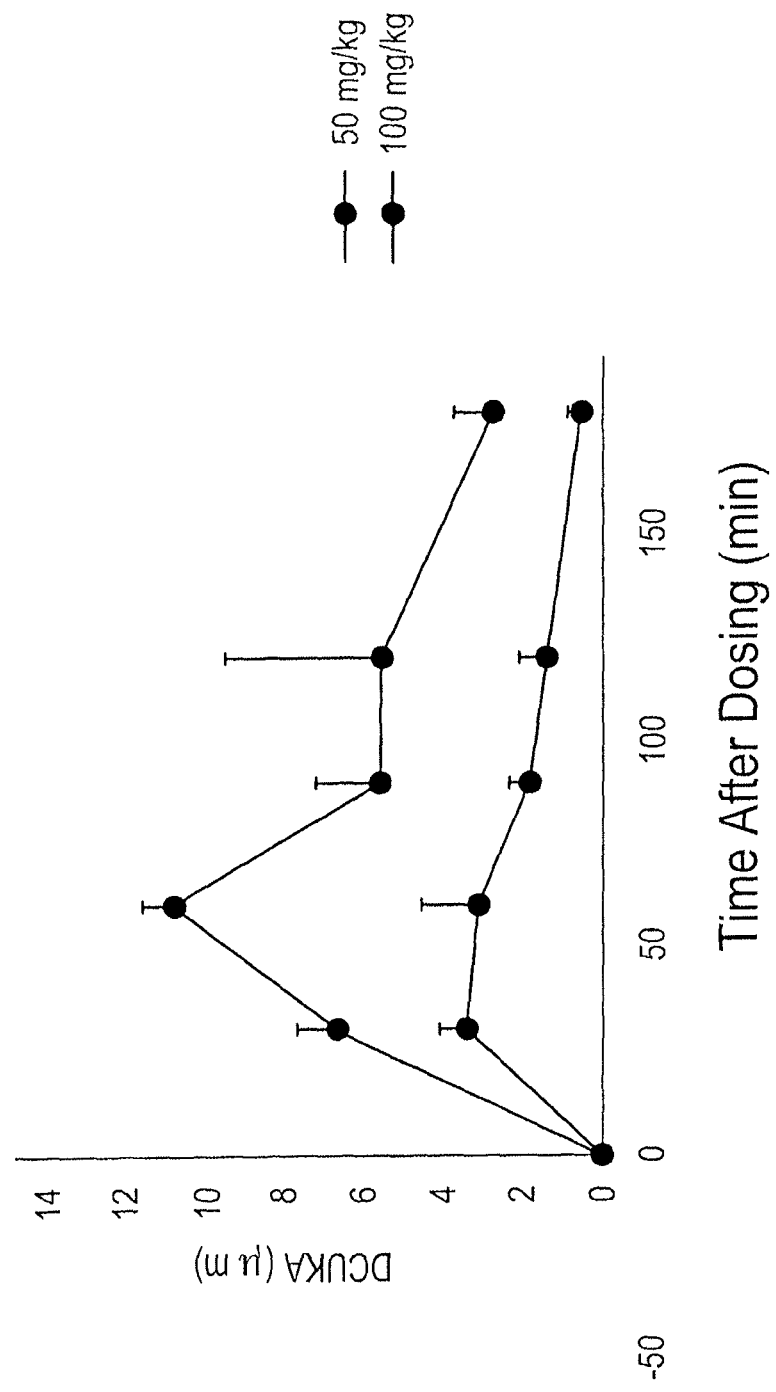
FIG. 1 graphically illustrates that DCUK-OEt can act as a pro-drug for DCUKA. When rats were administered DCUK-OEt orally in a suspension of a spray-dried dispersion formulation, the data show that the levels of DCUKA in blood depended on the dose of DCUK-OEt that was administered. The peak level of DCUKA is ~3 μM after the dose of 50 mg/kg of DCUK-OEt, and ~11 μM after the dose of 100 mg/kg of DCUK-OEt.

The analgesic compositions described herein are well suited for treatment of chronic (neuropathic) pain syndrome.

The methods described herein comprise treating a subject in need of pain relief (e.g., a human or animal patient) with the aminoquinoline containing compositions that also include an opioid, a NE/5-HT reuptake inhibitor, and/or a non-steroidal anti-inflammatory drug (NSAID).

Opioids suitable for use in the analgesic compositions include the opiates, i.e., the naturally occurring plant alkaloids such as morphine, codeine, papaverine, thebaine, and the like; the semi-synthetic opioids such as oxycodone, diamorphine, dihydrocodeine, and the like; as well as the synthetic opioids such as the phenylpyridine derivatives, e.g., 6-amino-5-(2,3,5-trichlorophenyl)-pyridine-2-carboxylic acid methylamide, and the like; the phenylpiperidine derivatives, e.g., fentanyl, sulfentanil, alfentanil, and the like; the morphinan derivatives, e.g., levorphanol, butorphanol, and the like; the diphenylheptane derivatives, e.g., methadone, propoxyphene, and the like; the benzomorphan derivatives, e.g., pentazocine, phenazocine, and the like.

Multitarget drugs suitable for use in analgesic compositions include drugs that act at the opiate receptor and/or at monoamine reuptake transporters, i.e., tramadol, and the like.

NSAIDs suitable for use in analgesic compositions include aspirin, the acetic acid derivatives such as indomethacin, sulindac, etodolac, tolmetin, ketorolac, nabumetone, diclofenac, and the like, the propionic acid derivatives such as ibuprofen, naproxen, fenoprofen, ketoprofen, flurbiprofen, oxaprozin, and the like, the enolic acid derivatives such as piroxicam, meloxicam, tenoxicam, and the like, the fenamic acid derivatives such as mefenamic acid, meclofenamic acid, flufenamic acid, and the like, as well as the pharmaceutically acceptable salts of the foregoing.

Illustrative NSAID salts suitable for use in the present compositions are the pharmaceutically acceptable salts of the aforementioned acetic acid derivatives, e.g., indomethacin salts such as indomethacin sodium, indomethacin meglumine, and the like, the tolmetin salts such as tolmetin sodium, and the like, ketorolac salts such as ketorolac tromethamine, and the like, diclofenac salts such as diclofenac sodium, diclofenac diethylamine, diclofenac epolamine, and the like, as well as pharmaceutically acceptable salts of the aforementioned propionic acid derivatives, e.g., ibuprofen salts such as ibuprofen lysine, ibuprofen methylglucamine, and the like, naproxen salts such as naproxen piperazine naproxen sodium, and the like, fenoprofen salts such as fenoprofen calcium, and the like.

The aminoquinoline compounds of Formula (I), (II), (III), (IV), (V) and (VI) can be prepared by any convenient method known to those skilled in the art. For example, U.S. Pat. No. 6,962,930 to Tabakoff et al. and U.S. Pat. No. 7,923,458 to Tabakoff, which are incorporated herein by reference in their entirety, describe the preparation of certain quinoline compounds analogous to those of the present invention, which readily can be adapted to the preparation of the desired aminoquinoline compounds. Scheme 1 provides a general scheme for preparing aminoquinoline compounds of Formula (I) and structurally related or analogous compounds from a 4-amino-substituted quinoline Compound (A), in which the R substituents are the same as those in Formula (I). The amino group of Compound (A) is reacted with an activated acylating Compound (B), comprising a leaving group (LG) that is reactive toward aromatic amino groups, to form a compound of Formula (I). Substituted quinoline compounds having an amino group in the 4-position of the quinoline ring structure, such as Compound (A), having various substitution patterns on the quinoline ring system, and the preparation thereof, are well known to those of ordinary skill in the chemical arts. Protective groups, such as those disclosed in *Protective Groups in Organic Synthesis,* 3rd Ed., Green and Wuts, Eds., John Wiley & Sons, Inc. (1999), which is incorporated herein by reference, can be utilized in the preparation of Compound (A), Compound (B) and/or in the coupling of Compound (A) and Compound (B), as needed or desired to facilitate the preparation and/or isolation of the compounds of Formula (I).

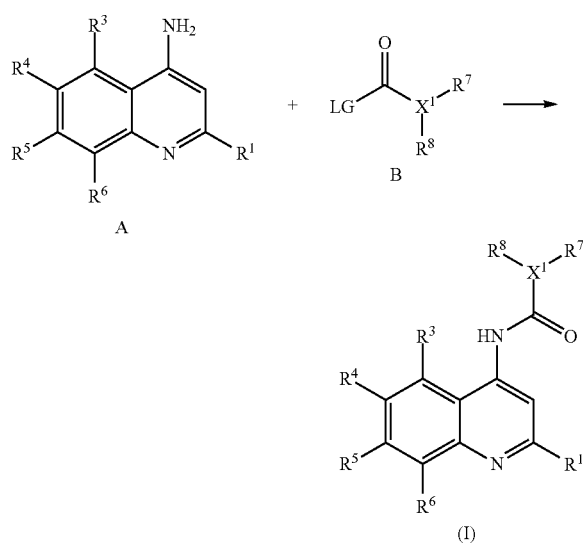

Scheme 1.

As used herein, the term "aminoquinoline compound" refers to compounds as set forth in Formulas (I), (II), (III), (IV), (V) and (VI) as described herein. The aminoquinoline compounds are useful for chronic pain and a variety of other conditions.

The term "alkyl" as used herein is directed to a saturated hydrocarbon group (designated by the formula $C_nH_{2n+1}$) which is straight-chained, branched or cyclized ("cycloalkyl") and which is unsubstituted or substituted, i.e., has had one or more of its hydrogens replaced by another atom or molecule.

"Aryl" designates either the 6-carbon benzene ring or the condensed 6-carbon rings of other aromatic derivatives (see, e.g., *Hawley's Condensed Chemical Dictionary* (13 ed.), R. J. Lewis, ed., J. Wiley & Sons, Inc., New York (1997)). Aryl groups include, without limitation, phenyl and naphthyl.

"Heteroaryl" rings are aromatic rings including at least one carbon atom in the ring and one or more, typically from 1-4, atoms forming the ring is an atom other than a carbon atom, i.e., a heteroatom (typically O, N or S). Heteroaryl includes, without limitation: morpholinyl, piperazinyl, piperidinyl, pyridyl, pyrrolidinyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, indolinyl, indolyl-4,7-dione, 1,2-dialkyl-indolyl, 1,2-dimethyl-indolyl, and 1,2-dialkyl-indolyl-4,7-dione.

"Alkoxy" means —OR where R is alkyl as defined above, e.g., methoxy, ethoxy, propoxy, 2-propoxy and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched divalent hydrocarbon radical of three to six carbon atoms, containing at least one triple bond, e.g., ethynyl, propynyl, and the like.

"Halide" and "halo" refer to a halogen atom including fluorine, chlorine, bromine, and iodine.

Substituent groupings, e.g., $C_{1-6}$ alkyl, are known, and are hereby stated, to include each of their individual substituent members, e.g., $C_1$ alkyl, $C_2$ alkyl, $C_3$ alkyl and $C_4$ alkyl.

"Substituted" means that one or more hydrogen atoms on the designated atom is/are replaced with a selection from the indicated group, provided that the designated atom's normal valency is not exceeded, and that the substitution results in a stable compound.

"Unsubstituted" atoms bear all of the hydrogen atoms dictated by their valency. When a substituent is, for example, "keto" then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

"Pharmaceutically acceptable", when used in reference to salts or carriers, refer to materials that are generally accepted as being suitable for administration to or contact with the human body or portions thereof. Pharmaceutically acceptable salts are materials in which the parent compound (e.g., an aminoquinoline compound of Formula (I)) or some other therapeutic agent or excipient is modified by making acid or base salts thereof. Examples of pharmaceutically-acceptable salts include, but are not limited to, mineral or organic acid salts of basic residues such as amines, or alkali or organic salts of acidic residues such as carboxylic acids. Pharmaceutically acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds, suitable for use in contact with the tissues of human beings and animals without causing excessive toxicity, irritation, allergic response, or other problems or complication, commensurate with a reasonable benefit/risk ratio.

Pharmaceutically acceptable salt forms of the aminoquinoline compounds provided herein are synthesized from the parent compound which contains a basic or acidic moiety by conventional chemical methods. Generally, such salts are prepared, for example, by reacting the free acid or base forms of these compounds with a stoichiometric amount of the appropriate base or acid in water or in an organic solvent, or in a mixture of the two. Generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is incorporated herein by this reference.

"Prodrugs" are any covalently bonded carriers which release the active parent drug of the aminoquinoline compounds in vivo when such prodrug is administered to a mammalian subject. Prodrugs of the aminoquinoline compounds of the present invention are prepared by modifying functional groups present in the compounds in such a way that the modifications are cleaved, either in routine manipulation or in vivo, including by enzymatic conversion, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples or prodrugs include, but are not limited to, acetate, formate and benzoate derivatives of alcohol and amine functional groups in the aminoquinoline compounds of the present invention, and the like. Compounds that function effectively as prodrugs of the aminoquinoline compounds of the present invention may be identified using routine techniques known in the art. For examples of such prodrug derivatives, see, for example, (a) Design of Prodrugs, edited by H. Bundgaard, (Elsevier, 1985) and *Methods in Enzymology,* Vol. 42, p. 309-396, edited by K. Widder et al. (Academic Press, 1985); (b) *A Textbook of Drug Design and Development*, edited by Krogsgaard-Larsen and H. Bundgaard, Chapter 5 "Design and Application of Prodrugs," by H. Bundgaard p. 113-191 (1991); (c) H. Bundgaard, *Advanced Drug Delivery Reviews,* 8, 1-38 (1992); (d) H. Bundgaard et al., *Journal of Pharmaceutical Sciences,* 77:285 (1988); and (e) N. Kakeya et al., *Chem. Pharm. Bull.,* 32: 692 (1984), each of which is specifically incorporated herein by reference.

In addition, the invention also includes solvates, metabolites, and pharmaceutically acceptable salts of the aminoquinoline compounds.

The term "solvate" refers to an aggregate of a molecule with one or more solvent molecules. A "metabolite" is a pharmacologically active product produced through in vivo metabolism in the body of a specified compound or salt thereof. Such products may result for example from the oxidation, reduction, hydrolysis, amidation, deamidation, esterification, deesterification, enzymatic cleavage, and the like, of the administered compound. Accordingly, the invention includes metabolites of the aminoquinoline compounds, including compounds produced by a process comprising contacting a compound of this invention with a mammal for a period of time sufficient to yield a metabolic product thereof.

Pharmaceutical Compositions and Treatment Regimens.

In one aspect, the instant invention provides pharmaceutical compositions which contain a pharmaceutically effective amount of the aminoquinoline compound together with an opioid or NSAID in a pharmaceutically acceptable carrier (e.g., a diluent, complexing agent, additive, excipient, adjuvant and the like). The aminoquinoline compositions can be present for example in a salt form, a micro-crystalline form, a nano-crystalline form, a co-crystalline form, a nanoparticulate form, a mirocparticulate form, and/or an amorphous form. The carrier can be an organic or inorganic carrier that is suitable for external, enteral or parenteral applications. The aminoquinoline compositions of the present invention can be compounded, for example, with the usual non-toxic, pharmaceutically acceptable carriers for tablets, pellets, capsules, liposomes, suppositories, intranasal sprays, solutions, emulsions, suspensions, aerosols, targeted chemical delivery systems, and any other form suitable for such use, which are well known in the pharmaceutical formulation arts. Non-limiting examples of carriers that can be used include water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, liquid or aerosol form. In addition auxiliary, stabilizing, thickening and coloring agents and perfumes can be used.

The pharmaceutical compositions comprise at least one aminoquinoline compound as described herein in combination with an opioid, NE- or 5HT uptake inhibitor and/or a NSAID and a pharmaceutically acceptable carrier, vehicle, or diluent, such as an aqueous buffer at a physiologically acceptable pH (e.g., pH 7 to 8.5), a polymer-based nanoparticle vehicle, a liposome, and the like. The pharmaceutical compositions can be delivered in any suitable dosage form, such as a liquid, gel, solid, cream, or paste dosage form. In one embodiment, the compositions can be adapted to give sustained release of the aminoquinoline compound.

In some embodiments, the pharmaceutical compositions include, but are not limited to, those forms suitable for oral, rectal, nasal, topical, (including buccal and sublingual), transdermal, vaginal, parenteral (including intramuscular, intraperitoneal, subcutaneous, and intravenous), spinal (epidural, intrathecal), and central (intracerebroventricular) administration. The compositions can, where appropriate, be conveniently provided in discrete dosage units. The pharmaceutical compositions of the invention can be prepared by any of the methods well known in the pharmaceutical arts. Some preferred modes of administration include intravenous (iv), topical, subcutaneous, oral and spinal. For systemic administration, the aminoquinoline compound generally will be administered the subject at a dosage in the range of about 1 milligram of aminoquinoline compound per kilogram of body mass (mg/kg) to about 200 mg/kg. Typically, the administered dosage should be sufficient to provide a concentration of aminoquinoline compound in the subject of about 100 nanomolar (nM) to about 100 micromolar (µM).

Pharmaceutical compositions suitable for oral administration include capsules, cachets, or tablets, each containing a predetermined amount of one or more of the aminoquinoline compounds, as a powder or granules. In another embodiment, the oral composition is a solution, a suspension, or an emulsion. Alternatively, the aminoquinoline compound containing analgesic compositions can be provided as a bolus, electuary, or paste. Tablets and capsules for oral administration can contain conventional excipients such as binding agents, fillers, lubricants, disintegrants, colorants, flavoring agents, preservatives, or wetting agents. The tablets can be coated according to methods well known in the art, if desired. Oral liquid preparations include, for example, aqueous or oily suspensions, solutions, emulsions, syrups, or elixirs. Alternatively, the compositions can be provided as a dry product for constitution with water or another suitable vehicle before use. Such liquid preparations can contain conventional additives such as suspending agents, emulsifying agents, non-aqueous vehicles (which may include edible oils), preservatives, and the like. The additives, excipients, and the like typically will be included in the compositions for oral administration within a range of concentrations suitable for their intended use or function in the composition, and which are well known in the pharmaceutical formulation art.

Pharmaceutical compositions for parenteral, spinal, or central administration (e.g. by bolus injection or continuous infusion) can be provided in unit dose form in ampoules, pre-filled syringes, small volume infusion, or in multi-dose containers, and preferably include an added preservative. The compositions for parenteral administration can be suspensions, solutions, or emulsions, and can contain excipients such as suspending agents, stabilizing agents, and dispersing agents. The additives, excipients, and the like typically will be included in the compositions for parenteral administration within a range of concentrations suitable for their intended use or function in the composition, and which are well known in the pharmaceutical formulation art. The aminoquinoline compounds are included in the compositions within a therapeutically useful and effective concentration range, as determined by routine methods that are well known in the medical and pharmaceutical arts.

Pharmaceutical compositions for topical administration to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like. The additives, excipients, and the like typically will be included in the compositions for topical administration to the epidermis within a range of concentrations suitable for their intended use or function in the composition, and which are well known in the pharmaceutical formulation art.

Pharmaceutical composition dosage forms suitable for buccal or sublingual administration include lozenges comprising the analgesic agents in a flavored base, such as sucrose, acacia, or tragacanth; pastilles comprising the aminoquinoline compound in an inert base such as gelatin and glycerin or sucrose and acacia; and mouthwashes comprising the active ingredient in a suitable liquid carrier. The pharmaceutical composition dosage forms for topical administration can include penetration enhancing agents, if desired. The additives, excipients, and the like typically will be included in the compositions of topical oral administration within a range of concentrations suitable for their intended use or function in the composition, and which are well known in the pharmaceutical formulation art. The analgesic agents are present in the compositions within a therapeutically useful and effective concentration range, as determined by routine methods that are well known in the medical and pharmaceutical arts.

For rectal administration the analgesic agents are provided in a solid or semisolid (e.g., cream or paste) carrier or vehicle. For example, such rectal compositions can be provided as unit dose suppositories. Suitable carriers or vehicles include cocoa butter and other materials commonly used in the art. The additives, excipients, and the like typically will be included in the compositions of rectal administration within a range of concentrations suitable for their intended use or function in the composition, and which are well known in the pharmaceutical formulation art.

The analgesic compositions of the present invention suitable for vaginal administration are provided as pessaries, tampons, creams, gels, pastes, foams, or sprays containing an aminoquinoline of the invention in combination with carriers as are known in the art. Alternatively, compositions suitable for vaginal administration can be delivered in a liquid or solid dosage form. The additives, excipients, and the like typically will be included in the compositions of vaginal administration within a range of concentrations suitable for their intended use or function in the composition, and which are well known in the pharmaceutical formulation art.

Analgesic compositions suitable for intra-nasal administration are also encompassed by the present invention. Such intra-nasal compositions comprise, in addition to the analgesic agents, a delivery vehicle and a suitable device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising the aminoquinoline. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of the aminoquinoline. Alternatively, pharmaceutical compositions for administration by inhalation or insufflation can be provided in the form of a dry powder composition, for example, a powder mix of the analgesic agents and a suitable powder base such as lactose or starch. Such powder composition can be provided in unit dosage form, for example, in capsules, cartridges, gelatin packs, or blister packs, from which the powder can be administered with the aid of an inhalator or insufflator. The additives, excipients, and the like typically will be included in the compositions of intra-nasal administration within a range of concentrations suitable for their intended use or function in the composition, and which are well known in the pharmaceutical formulation art.

Methods for alleviating chronic pain (e.g., neuropathic pain) comprise administering to a patient suffering from one of the aforementioned conditions an effective amount of an aminoquinoline compound together with an opioid and/or a NSAID and/or 5-HT/NE uptake inhibitor. Preferably, the analgesic composition is administered parenterally or enterally. The dosage of the effective amount of the aminoquinoline compounds can vary depending upon the age and condition of each individual patient to be treated. Suitable dosages of the aminoquinoline compound typically range about 1 mg/kg to about 200 mg/kg, and the aminoquinoline compound can be administered together with an opioid, NSAID and/or 5-HT/NE uptake inhibitor at one tenth to the full recommended dose of a particular compound. Such dosages can be administered one or more times a day, one or more times a week, one or more times per month, and the like.

As used herein, the terms "reducing", "inhibiting", "blocking", "preventing", "alleviating", "relieving", and "antagonist", when referring to a composition mean that the compound brings down the occurrence, severity, size, volume, or associated symptoms of a condition, event, or activity by at least about 7.5%, 10%, 12.5%, 15%, 17.5%, 20%, 22.5%, 25%, 27.5%, 30%, 35%, 40%, 45%, 50%, 55%, 60%, 65%, 70%, 75%, 80%, 90%, or 100% compared to how the condition, event, or activity would normally exist without application of the composition comprising the compound. The terms "increasing", "elevating", "enhancing", "upregulating", "improving", "activating" and "agonist", when referring to a compound mean that the compound increases the occurrence or activity of a condition, event, or activity by at least about 7.5%, 10%, 12.5%, 15%, 17.5%, 20%, 22.5%, 25%, 27.5%, 30%, 35%, 40%, 45%, 50%, 55%, 60%, 65%, 70%, 75%, 80%, 90%, 100%, 150%, 200%, 250%, 300%, 400%, 500%, 750%, or 1000% compared to how the condition, event, or activity would normally exist without application of the composition.

The following examples are included to demonstrate certain aspects of the invention. It should be appreciated by those of skill in the art that the techniques disclosed in the examples, which represent techniques known to function well in practicing the invention, can be considered to constitute preferred modes for its practice. However, those of skill in the art should, in light of the present disclosure, appreciate that many changes can be made in the specific disclosed embodiments and still obtain a like or similar result without departing from the spirit and scope of the invention. The examples are provided for illustration purposes only and are not intended to be limiting.

Methods of Ascertaining Potentiation/Synergism.

Although the definition of potentiation/synergism in drug effects is relatively simple, the approaches to show synergy have not always been agreed upon. A review of methodology by Foucquier and Gued (2015) focuses on analytical approaches for measuring efficacy of drug combinations, and presents a succinct description of currently used methods. The methods are divided into an "Effect-Based Strategy" which consists of four approaches: (1) Combination Subthresholding; (2) Highest Single Agent Approach; (3) Response Additivity and (4) The Bliss Independence Model; and a "Dose-Effect Based Strategy", which was first described by Loewe (1926) and is currently referred to as isobolographic analysis (Tallarida 2001). Within this "Effect-Based Strategy" all four approaches have been utilized to test for potentiation/synergy with the described drug combinations. All four approaches produced coincident results.

Use of DCUKA to Increase Potency of Opioids/NSAIDs/5-HT and NE Reuptake Inhibitors.

The data below demonstrate that a dose of DCUKA equivalent to a threshold dose for reducing chronic pain in a rat model of chronic inflammatory pain (Freund's Adjuvant Model) or a rat model of osteoarthritis (MIA), when administered with a low dose of opioid, NSAID or a compound which reduces pain by inhibiting synaptic uptake of norepinephrine and/or serotonin (e.g., Tramadol), increases the potency of the opioid, NSAID and/or the serotonin/norepinephrine reuptake inhibitors in reducing chronic pain. Regarding opioids other than morphine, the standard of the "Morphine Equivalent Dose Measure" or "Morphine Milligram Equivalents" (MME) can be utilized to ascertain the amount of another analgesic equipotent to a particular daily dose of morphine. The administration of DCUKA, or DCUK-OEt (which acts as a prodrug for DCUKA), together with morphine increases the potency of morphine by 4-5 fold. Using the MME to calculate the dose of another analgesic to be given on a daily basis (based on dose and the number of times this dose of analgesic in question is administered per day), addition of DCUKA or DCUK-OEt to the pain treatment allows the analgesic dose to be reduced in the same manner as the reduction of the morphine dose when morphine is given with DCUKA/DCUK-OEt.

Calculation of the Dose of Analgesic to be Given when Using DCUKA or DCUK-OEt to Potentiate Analgesic Action.

The dose of another analgesic when given with DCUKA can be calculated by the following formula:

Dose of opioid analgesic=daily dose of morphine used in a similar situation÷MME÷A factor based on the increase in opioid potency as a result of addition of DCUKA or DCUK-OEt.

As an example, to calculate the dose of oxycodone the following information is used: (1) The MME for the opioid of interest (in this case oxycodone) is 1.5 (Von Korff et al., Clin. J. Pain 24(6):521-527 (2008)); (2) the daily dose of morphine needed to treat the level of pain reported by the patient. The use of rating scales is important in this regard (Schneider et al., 2003). For moderate to severe pain, a singular dose of morphine (oral) can vary between 10 and 30 mg and such doses are taken 6 times daily (i.e., 60-180 mg/day); (3) the factor by which the dose of opioid can be decreased by addition of DCUKA to the dosing regimen for pain.

For humans, the dose of DCUKA can vary between 150-450 mg given 2-3 times per day. If DCUKA is administered as such, the dose of the opioid that is used can be lowered by a factor of 4-5 (this factor is determined based on data in FIGS. 11 and 12. The pain treatment specialist should closely monitor the patient to adjust dosing as necessary for the comfort of the patient. This can be accomplished by increasing the dose of opioid or DCUKA within the recommended ranges.

Examples of Actual Dose Calculations

Starting dose of oxycodone/day=(60 mg[morphine daily starting dose])÷(1.5[MME])÷(5=opioid lowering factor)=8 mg/day.

Starting dose of methadone/day=(60)÷(4)÷(5)=3 mg/day.

Methadone given for control of pain is usually titrated upward over a six-week period and the lower dose given with DCUKA can be titrated accordingly.

Similar calculations can be made for other opioids approved for use with humans for the treatment of chronic pain syndromes. It should be clear to those trained in the art, that there are significant differences among individuals in the amount of pain perceived, and the perceived pain also varies with the cause of the pain and extent of injury. The given examples are illustrations of what can be considered a method of maintaining the level of analgesia/antihyperalgesia while lowering doses of opioids in conjunction with administration of DCUKA. If necessary to further control pain, the daily dose of DCUKA and/or opioid can be incrementally increased (an increment would involve a 25-50% increase in daily dose of DCUKA or opioid).

For use with NSAIDs together with DCUKA the same principles apply, except the factor by which the dose of NSAID can be reduced when given together with DCUKA is in the range of about 5 to about 6.

Daily dose of diclofenac=(60 mg[daily morphine dose])÷(0.10)÷(6)=100 mg.

For humans taking diclofenac sodium the recommendation is not to exceed 225 mg/day.

Thus, based on the discovery that DCUKA and its prodrug (DCUK-OEt), can increase the potency of opioids and NSAIDs, a downward adjustment of the daily doses of opioids and NSAIDs results in lowering of side effects while maintaining pain relief.

In the absence of published MEE values for the NE/5-HT reuptake inhibitors one can use the data we have presented on the effects of tramadol given in conjunction with DCUKA for treatment of osteoarthritis (FIG. 9). Tramadol has been shown to be a weak opioid, but to have substantial effects as a NE/5-HT reuptake inhibitor (Barber, 2011). Other NE/5-HT reuptake inhibitors are duloxetine, venlafaxine, milnacipran, and the like. The data indicate that one can reduce the dose of the NE/5-HT reuptake inhibitor by one half when given together with 150-450 mg DCUKA to humans two to three doses/day.

Example 1. Preparation of Compounds of Formula (VI)

Derivatives of kynurenic acid containing a tertiary ureido group, including 5,7-dichloro-4-(3,3-diphenylureido)quinoline-2-carboxylic acid (DCUKA, 7a), may be synthesized, as previously described (Snell et al., 2000) through the use of a reactive carbamoyl chloride intermediate (6a-b). However, it is possible to achieve an improvement on this synthesis due to concomitant ester hydrolysis during the final acylation reaction. One compound embodiment, 5,7-dichloro-4-(3,3-dibutylureido)quinoline-2-carboxylic acid (BCUKA, 7b), was synthesized via this method in the synthesis phases I-IV as explained and illustrated in Scheme 2 (Reagents and conditions (I): MeOH, reflux, 16 h. (II): Ph₂O, 250° C., 2 h. (III): (a) C₁SO₂NCO, MeCN, reflux, 2 h. (b) HCl, MeOH, RT, 30 min. (IV): NaH, DMF, 0° C. to RT, 16 h).

Scheme 2.

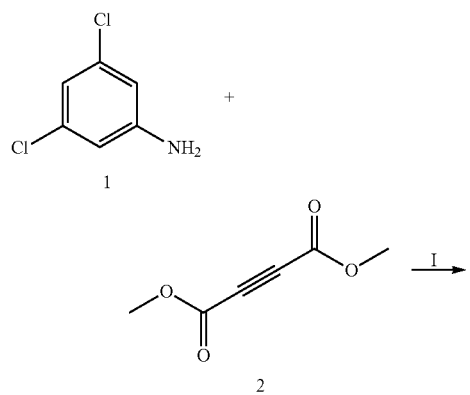

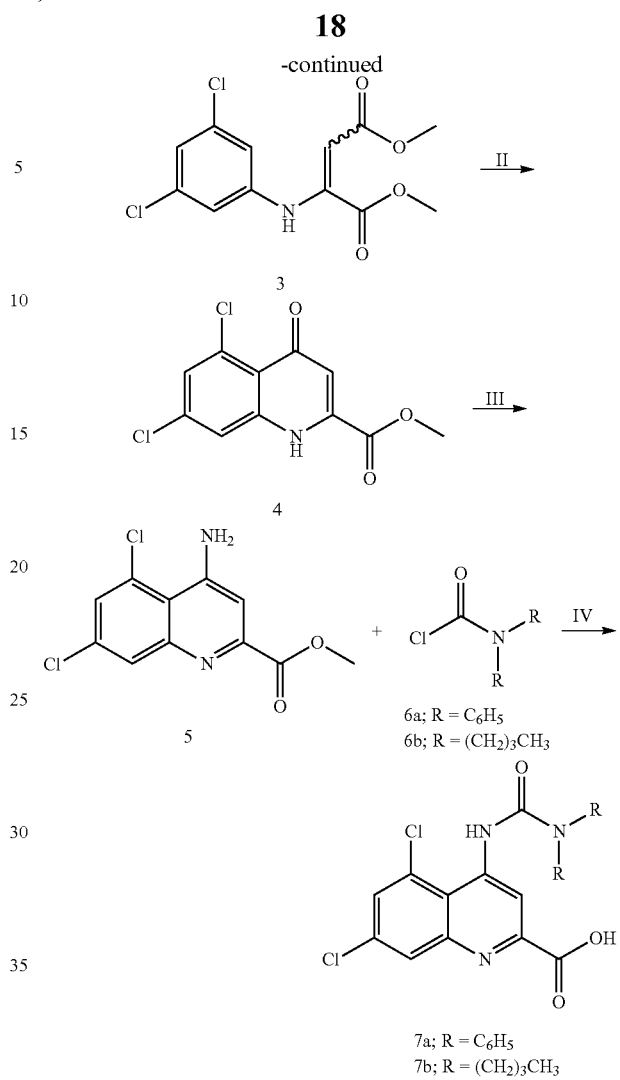

Synthesis Phase I 3,5-Dichloroaniline (1, 5.00 g, 30.9 mmol) and dimethyl acetylenedicarboxylate (2, 3.80 ml, 30.9 mmol) were combined in anhydrous MeOH (60 ml) under nitrogen, and refluxed for 16 hours. The reaction mixture was cooled to room temperature and evaporated to dryness. The resulting yellow solid was recrystallized from MeOH (twice) to give a mixture of cis and trans isomers of the target dimethyl anilinomaleate (3) as thin yellow crystals (5.23 g, 17.2 mmol). The absorption peak values (in ppm) found in the $^1$H NMR spectrum performed in deuterated DMSO were 3.57 & 3.67 (3H, s), 3.72 & 3.80 (3H, s), 5.35 & 5.58 (1H, s), 6.98 & 7.12 (2H, $s_{app}$), 7.23 & 7.31 (1H, $s_{app}$), 9.52 & 9.64 (1H, br, s).

Synthesis Phase II

Dimethyl anilinomaleate (3, 3.50 g, 11.5 mmol) was added portion-wise to diphenyl ether (70 ml) at 250° C. The temperature of the resulting solution was maintained at 250° C. for 2 hours, before being cooled to room temperature and diluted with hexanes (100 ml). The resultant precipitate was removed by filtration, washed with hexanes (50 ml), and suspended in refluxing ethanol, before being filtered to remove soluble impurities. The solid filtrand was dried under vacuum to give the desired quinolone carboxylate (4) as an off-white solid (3.10 g, 11.4 mmol). The absorption peak values (in ppm) found in the $^1$H NMR spectrum performed in deuterated DMSO were 3.96 (3H, s), 6.59 (1H, s), 7.42 (1H, s), 7.97 (1H, s), 12.05 (1H, br). This process can be adapted for use with a continuous flow apparatus (Cao, 2017) to mitigate against the high temperatures in the presence of diphenyl ether.

Synthesis Phase III

Chlorosulfonyl isocyanate (1.20 ml, 13.8 mmol) was added to a slurry of quinoline carboxylate (4, 2.50 g, 9.19 mmol) in anhydrous MeCN (35 ml) at room temperature. The mixture was brought to reflux for 1.5 hours, at which point the heating was stopped and a 1.0 M solution of HCl in anhydrous MeOH (20 ml) was added. The reaction mixture was allowed to cool to room temperature with stirring until a precipitate formed after 1 hour. The precipitate was removed via filtration, washed with MeCN, and air dried. The filter cake was suspended in water (50 ml) to which saturated sodium carbonate solution (~5 ml) was added to pH 10, causing thickening of the suspension. The resultant solid was collected by filtration, washed with cold water and dried under vacuum (40° C.) to give the target aminoquinoline (5) as an off-white solid (1.82 g, 6.71 mmol). The absorption peak values (in ppm) found in the $^1$H NMR spectrum performed in deuterated DMSO were 4.05 (3H, s), 6.04 (2H, s), 7.33 (1H, s), 7.47 (1H, d, J=1.9 Hz), 8.10 (1H, d, J=1.9 Hz).

Synthesis Phase IV

The acylation of aminoquinoline (5), with concomitant ester hydrolysis, to yield 5,7-dichloro-4-(3,3-dibutylureido)quinoline-2-carboxylic acid (BCUKA, 7b) was performed as follows; N,N-dibutylcarbamoyl chloride (6b, 96 mg, 0.50 mmol) and aminoquinoline (5, 113 mg, 0.42 mmol) were dissolved in anhydrous DMF (2 ml) and cooled to 0° C. Sodium hydride dispersion in mineral oil (60%, 35 mg, 0.83 mmol) was added and the mixture was allowed to warm to room temperature and stirred for 16 hours. The reaction was quenched via addition to saturated NH$_4$Cl solution (1 ml), followed by adjustment to pH 3 with 1.0M aqueous HCl. Extraction with EtOAc (2×10 ml) followed by washing with saturated brine (5 ml) and drying (Na$_2$SO$_4$) gave the crude product as a pale yellow oil. Compound purification via silica gel chromatography (9:1 DCM:MeOH) gave 5,7-dichloro-4-(3,3-dibutylureido)quinoline-2-carboxylic acid (DBCUKA, 7b) as a pale yellow solid (82 mg, 0.20 mmol). The absorption peak values (in ppm) found in the $^1$H NMR spectrum performed in CDCl$_3$ were 1.00 (6H, t, J=7.4 Hz), 1.36-1.45 (4H, m), 1.64-1.72 (4H, m), 3.39-3.45 (4H, m), 5.17 (1H, s), 7.69 (1H, s), 8.30 (1H, s), 9.16 (1H, s).

Carbamoyl chlorides are limited in their commercial availability, and, furthermore, are characterized by high reactivity, especially to hydrolysis, and subsequent poor stability. This is particularly evident in the case of mono-n-substituted carbamoyl chlorides. Therefore, in order to prepare mono-n-substituted analogues of kynurenic acid it was advantageous to utilize alternative carbamoyl cation equivalents, with attenuated reactivity. Carbamoyl imidazoles (e.g. 9a-d) have been shown to be suitable reactive species for the synthesis of a variety of functional groups including ureas, thioureas, carbamates, thiocarbamates and amides. (Grzyb et al., 2005) Derivatives of kynurenic acid containing a secondary ureido group were prepared using this approach in synthesis phases V-VII as explained and illustrated in Scheme 3 (Reagents and conditions: (V): CDI, DCM, 0° C. to RT, 16 h. (VI): 5, NaH, DMF, 0° C. to RT, 16 h. (VII) TFA, DCM, RT, 16 h.).

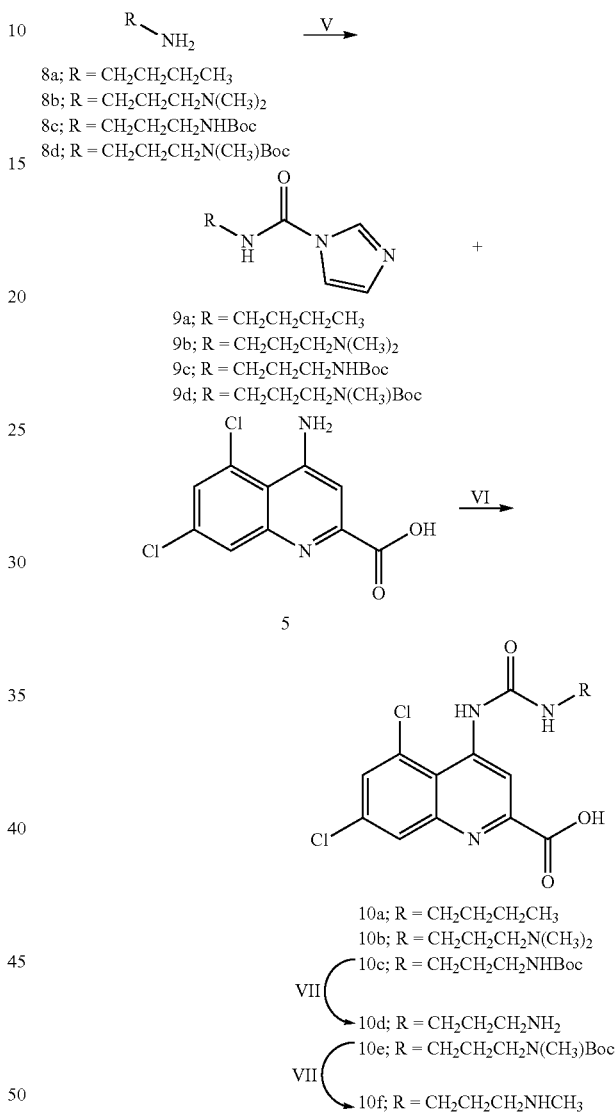

General Example of Synthesis Phase V n-Butylamine (8a, 100 µl, 74 mg, 1.01 mmol) in DCM (1 ml) was added to a solution of CDI (0.197 g, 1.21 mmol) in DCM (5 ml) at 0° C., before the reaction mixture was allowed to warm to RT and stirred overnight. The solution was diluted with DCM (10 ml) washed with water (2×10 ml) and brine (10 ml), dried (Na$_2$SO$_4$) and evaporated to dryness to give the target carbamoyl imidazole (9a) as a colorless oil (115 mg, 0.69 mmol). The absorption peak values (in ppm) found in the $^1$H NMR spectrum performed in CDCl$_3$ were 0.97 (3H, t, J=7.4 Hz), 1.42 (2H, qt, J=7.6, 7.3 Hz), 1.63 (2H, tt, J=7.3, 7.0 Hz), 3.44 (2H, dt, J=7.0, 6.7 Hz), 6.75 (1H, br), 7.07 (1H, s), 7.42 (1H, s), 8.17 (1H, s).

N-(3-(Dimethylamino)propyl)-1H-imidazole-1-carboxamide (9b) was prepared from 3-dimethylaminopropylamine (8b) as described in synthesis phase V. The absorption peak values (in ppm) found in the $^1$H NMR spectrum performed in CDCl$_3$ were 1.77 (2H, tt, J=5.7, 5.5 Hz), 2.32 (6H, s), 2.56 (2H, t, J=5.5 Hz), 3.54 (2H, dt, J=5.9, 5.5 Hz), 7.07 (1H, s), 7.27 (1H, s), 8.04 (1H, s), 9.34 (1H, br).

tert-Butyl (3-(1H-imidazole-1-carboxamido)propyl)carbamate (9c) was prepared from tert-butyl (3-aminopropyl) carbamate (8c) as described in synthesis phase V. The absorption peak values (in ppm) found in the $^1$H NMR spectrum performed in CDCl$_3$ were 1.49 (9H, s), 1.73 (2H, tt, J=5.8, 5.7 Hz), 3.30 (2H, dt, J=6.4, 5.7 Hz), 3.48 (2H, dt, J=6.0, 5.8 Hz), 4.91 (1H, br), 7.11 (1H, s), 7.52 (1H, s), 7.92 (1H, br), 8.25 (1H, s).

tert-Butyl (3-(1H-imidazole-1-carboxamido)propyl)(methyl)carbamate (9d) was prepared from V-(3-aminopropyl)-N-methylcarbamic acid tert-butyl ester (8d) as described in synthesis phase V. The absorption peak values (in ppm) found in the $^1$H NMR spectrum performed in CDCl$_3$ were 1.49 (9H, s), 1.74-1.80 (2H, br), 2.87 (3H, s), 3.35-3.43 (4H, m), 7.09 (1H, s), 7.53 (1H, s), 8.11 (1H, br), 8.25 (1H, s).

General Example of Synthesis Phase VI

It was possible to use carbamoyl imidazoles (9a-d) in a manner analogous to carbamoyl chlorides in synthesis phase IV, allowing for a single step involving acylation of the amino quinoline (5) and simultaneous ester hydrolysis. The approach was utilized for the synthesis of 4-(3-butylureido)-5,7-dichloroquinoline-2-carboxylic acid (10a) as follows; N-butyl-1H-imidazole-1-carboxamide (9a, 125 mg, 0.95 mmol) and aminoquinoline (5, 215 mg, 0.79 mmol) were dissolved in anhydrous DMF (4 ml) and cooled to 0° C. Sodium hydride dispersion in mineral oil (60%, 63 mg, 1.58 mmol) was added and the mixture was allowed to warm to room temperature and stirred for 16 hours. The reaction was quenched via addition to saturated NH$_4$Cl solution (3 ml), followed by adjustment to pH 3 with 1.0 M aqueous HCl. Extraction with EtOAc (2×20 ml) followed by washing with saturated brine (10 ml) and drying (Na$_2$SO$_4$) gave the crude product as a pale orange residue. Compound purification via reverse phase (C$_{18}$) silica gel chromatography (1:1 H$_2$O:MeCN) gave 4-(3-butylureido)-5,7-dichloroquinoline-2-carboxylic acid (10a) as a beige solid (142 mg, 0.39 mmol). The absorption peak values (in ppm) found in the $^1$H NMR spectrum performed in deuterated DMSO were 0.92 (3H, t, J=7.3 Hz), 1.31-1.38 (2H, m), 1.44-1.52 (2H, m), 3.16 (2H, dt, J=6.6, 6.0 Hz), 7.47 (1H, br), 7.87 (1H, d, J=2.2 Hz), 8.11 (1H, d, J=2.2 Hz), 8.68 (1H, s), 9.12 (1H, br).

5,7-Dichloro-4-(3-(3-(dimethylamino)propyl)ureido)quinoline-2-carboxylic acid (10b) was prepared from N-(3-(dimethylamino)propyl)-1H-imidazole-1-carboxamide (9b) as described in synthesis phase VI. Due to the zwitterionic nature of the target compound, acidification to pH ½ was performed with TFA prior to reverse phase (C18) chromatography to afford the product as the TFA salt form. The absorption peak values (in ppm) found in the $^1$H NMR spectrum performed in D$_2$O were 1.87-2.00 (2H, m), 2.87 (6H, s), 3.12-3.20 (2H, m), 3.21-3.31 (2H, m), 7.13 (1H, s), 7.48 (1H, s), 8.06 (1H, s). The absorption peak value (in ppm) found in the $^{19}$F NMR spectrum performed in D$_2$O was −75.6.

4-(3-(3-((tert-Butoxycarbonyl)amino)propyl)ureido)-5,7-dichloroquinoline-2-carboxylic acid (10c) was prepared from tert-butyl (3-(1H-imidazole-1-carboxamido)propyl) carbamate (9c) as described in synthesis phase VI. The absorption peak values (in ppm) found in the $^1$H NMR spectrum performed in deuterated DMSO were 1.39 (9H, s), 1.60 (2H, tt, J=6.8, 6.6 Hz), 2.95-3.02 (2H, m), 3.12-3.18 (2H, m), 6.83 (1H, br), 7.45 (1H, br), 7.85 (1H, s), 8.10 (1H, s), 8.65 (1H, s), 9.15 (1H, br).

4-(3-(3-((tert-Butoxycarbonyl) (methyl)amino)propyl) ureido)-5,7-dichloroquinoline-2-carboxylic acid (10e) was prepared from tert-butyl (3-(1H-imidazole-1-carboxamido) propyl)methyl carbamate (9d) as described in synthesis phase VI. The absorption peak values (in ppm) found in the $^1$H NMR spectrum performed in deuterated DMSO were 1.39 (9H, s), 1.63-1.71 (2H, m), 2.79 (3H, s), 3.08-3.16 (2H, m), 3.19-3.26 (2H, m), 7.27 (1H, br), 7.68 (1H, d, J=1.8 Hz), 8.29 (1H, d, J=1.8 Hz), 8.40 (1H, br), 8.97 (1H, br).

General Example of Synthesis Phase VII

TFA (173 µL, 2.25 mmol) was added to a solution of Boc-protected amine (10c, 103 mg, 0.23 mmol) in DCM (4 ml). After stirring at room temperature for 16 hours, the solvent was removed under reduced pressure and the residue was purified directly by reverse phase chromatography (C$_{18}$, 1:1 H$_2$O:MeCN) to give the TFA salt form of 4-(3-(3-aminopropyl)ureido)-5,7-dichloroquinoline-2-carboxylic acid (10d) as a white solid (64 mg, 0.14 mmol). The absorption peak values (in ppm) found in the $^1$H NMR spectrum performed in D$_2$O (1.0% TFA) were 1.61 (2H, tt, J=6.9, 7.1 Hz), 2.72 (2H, t, J=7.1 Hz), 3.04 (2H, t, J=6.9 Hz), 7.62 (1H, s), 7.89 (1H, s), 8.71 (1H, s).

5,7-Dichloro-4-(3-(3-(methylamino)propyl)ureido)quinoline-2-carboxylic acid (10f) was prepared from 4-(3-(3-((tert-Butoxycarbonyl)(methyl)amino)propyl)ureido)-5,7-dichloroquinoline-2-carboxylic acid (10e) as described in synthesis phase VI. The absorption peak values (in ppm) found in the $^1$H NMR spectrum performed in D$_2$O (1.0% TFA) were 1.81 (2H, tt, J=6.8, 7.7 Hz), 2.55 (3H, s), 2.94 (2H, t, J=7.8 Hz), 3.22 (2H, t, J=6.8 Hz), 7.78 (1H, d, J=1.9 Hz), 8.01 (1H, d, J=1.9 Hz), 8.77 (1H, s). The absorption peak value (in ppm) found in the $^{19}$F NMR spectrum performed in D$_2$O was −73.4. The compound structures are shown in Scheme 4.

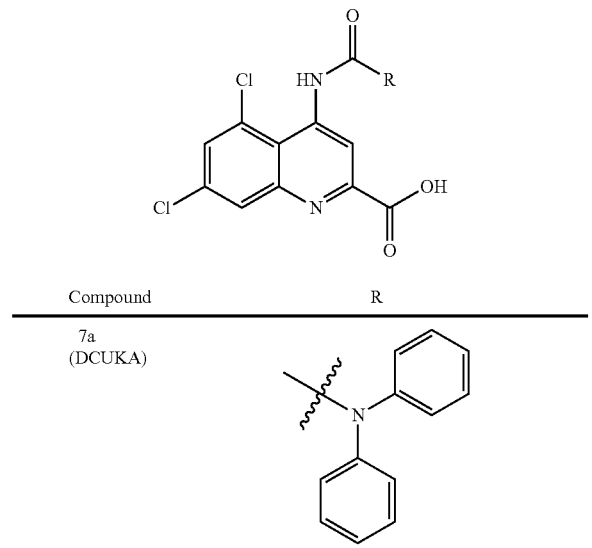

Scheme 4.

Scheme 4.

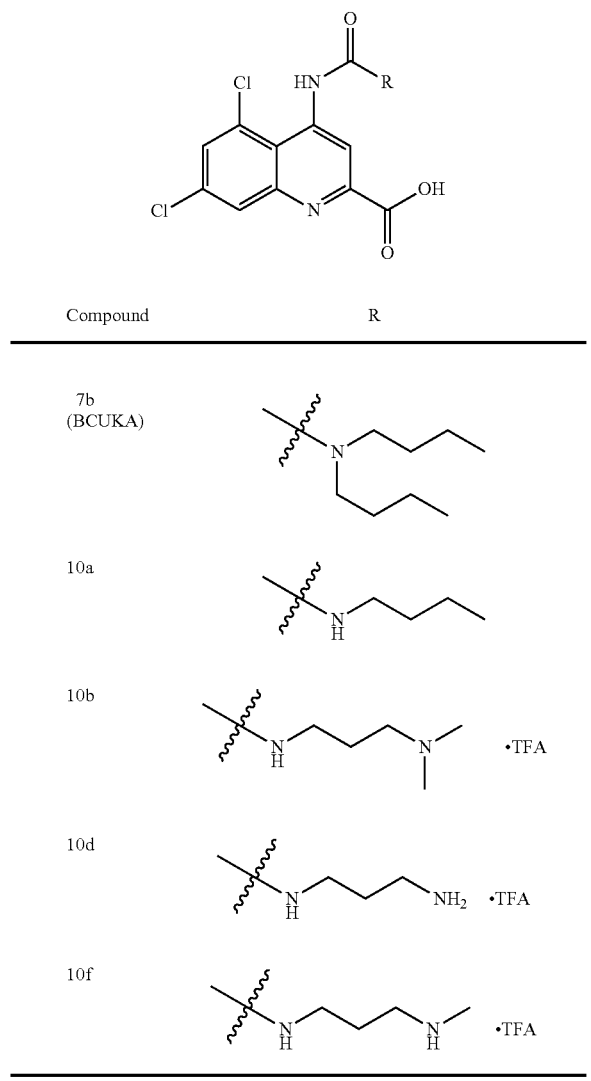

| Compound | R |
|---|---|
| 7b (BCUKA) | N-dibutyl |
| 10a | NH-butyl |
| 10b | NH-CH2CH2CH2-N(CH3)2 ·TFA |
| 10d | NH-CH2CH2CH2-NH2 ·TFA |
| 10f | NH-CH2CH2CH2-NH-CH3 ·TFA |

Synthesis of 3-(2-butyryl-5,7-dichloroquinolin-4-yl)-1,1-diphenylurea

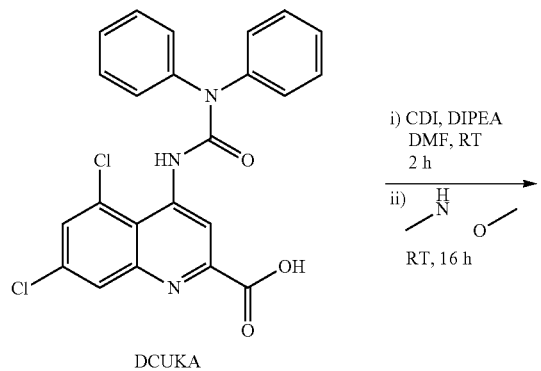

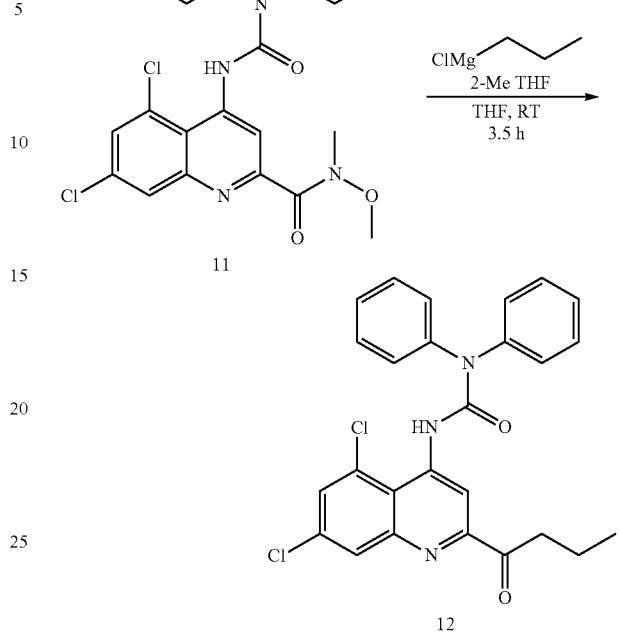

A. 5,7-Dichloro-4-(3,3-diphenylureido)-N-methoxy-N-methylquinoline-2-carboxamide (11)

Carbonyldiimidazole (72 mg, 0.44 mmol) and diisoproylethylamine (115 uL, 0.66 mmol) were added to a solution of 5,7-dichloro-4-(3,3-diphenylureido)quinoline-2-carboxylic acid (DCUKA; 100 mg, 0.22 mmol) in dry N,N-dimethylformamide (15 mL). The reaction mixture was stirred at room temperature under nitrogen for 2 hours, before N,O-dimethylhydroxylamine hydrochloride (86 mg, 0.88 mmol) was added. The resulting pale yellow solution was stirred at room temperature for a further 16 hours, at which point the solvent was removed under reduced pressure and the residue was dissolved in ethyl acetate (20 mL) and washed with saturated sodium hydrogen carbonate solution (2×15 mL) and 0.1M HCl (2×15 mL), followed by water (15 mL) and brine (10 mL). The organic phase was dried (MgSO$_4$) and evaporated to dryness. The target compound was obtained following purification by chromatography on silica (1:1 Hexanes:EtOAc) as a white solid (81 mg, 0.16 mmol, 73%). Rf 0.33 (1:1 Hexanes:EtOAc); M.p. 207-210° C.; 1H NMR (400 MHz, CDCl$_3$) 3.40 (3H, s), 3.75 (3H, br), 7.28 (1H, s), 7.34-7.37 (2H, m), 7.41-7.49 (8H, m), 8.03 (1H, d, J=2.0 Hz), 8.87 (1H, s), 9.39 (1H, s).

B. 3-(2-Butyryl-5,7-dichloroquinolin-4-yl)-1,1-diphenylurea (12)

A n-Propylmagnesium chloride solution in 2-methyltetrahydroduran (1.0M, 1.12 mL, 1.12 mmol) was added dropwise to a solution of 5,7-dichloro-4-(3,3-diphenylureido)-N-methoxy-N-methylquinoline-2-carboxamide (11, 70 mg, 0.14 mmol) in dry tetrahydrofuran (10 mL) at −10° C., under nitrogen. Following addition, the reaction mixture was stirred at −10° C. for 30 min, before being allowed to warm to room temperature and stirred for an additional 3 hrs. The reaction was quenched with saturated ammonium chloride solution (10 mL) and the product, ketone 12, was extracted with ethyl acetate (3×15 mL). The organic extract was washed with brine (10 mL) and dried (MgSO$_4$) before being evaporated to dryness. The residue was purified via chromatography on silica (4:1 Hexanes:EtOAc) to afford the target compound as a pale yellow solid (32 mg, 0.07 mmol, 47%). Rf 0.45 (4:1 Hexanes:EtOAc); M.p. 161-164° C.; 1H NMR (400 MHz, CDCl$_3$) 1.03 (3H, t, J=7.4 Hz), 1.80 (2H, qt, J=7.3, 7.4 Hz), 3.24 (2H, t, J=7.3 Hz), 7.28 (1H, s), 7.34-7.38 (2H, m), 7.42-7.49 (8H, m), 8.09 (1H, d, J=2.1 Hz), 9.15 (1H, s), 9.31 (1H, s).

Synthesis of 5,7-dichloro-4-(3,3-diphenylureido)-N-ethylquinoline-2-carboxamide (13)

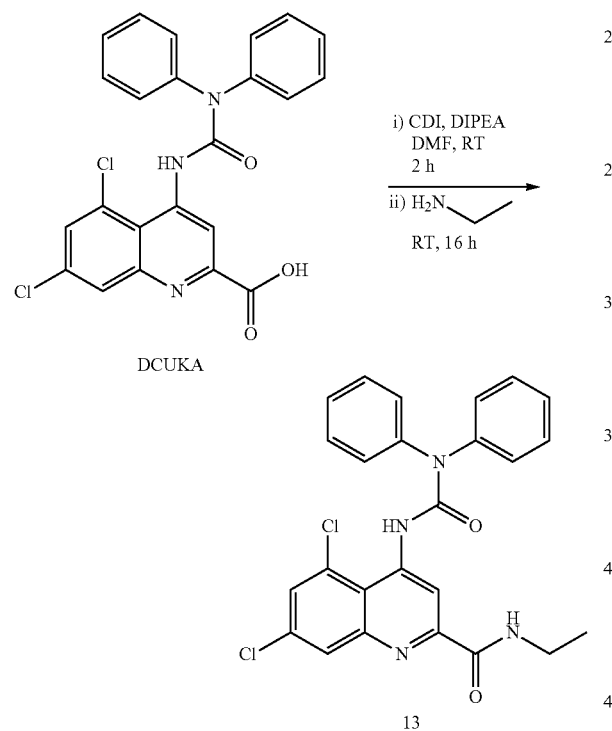

Carbonyldiimidazole (143 mg, 0.88 mmol) and diisoproylethylamine (230 uL, 1.32 mmol) were added to a solution of 5,7-dichloro-4-(3,3-diphenylureido)quinoline-2-carboxylic acid (DCUKA; 200 mg, 0.44 mmol) in dry N,N-dimethylformamide (25 mL). The reaction mixture was stirred at room temperature under nitrogen for 2 hours, before ethylamine in THF (2.0M, 0.66 mL, 1.32 mmol) was added. The resulting pale yellow solution was stirred at room temperature for a further 16 hours, at which point the reaction was complete. The solvent was removed under reduced pressure and the residue was dissolved in ethyl acetate (50 mL) and washed with saturated sodium hydrogen carbonate solution (2×30 mL) and 0.1M HCl (2×30 mL), followed by water (25 mL) and brine (25 mL). The organic phase was dried (MgSO$_4$) and evaporated to dryness. The target ethylamide 13 was via silica gel chromatography (1:1 Hexanes:EtOAc) as an off-white solid (148 mg, 0.31 mmol, 71%). Rf 0.43 (1:1 Hexanes:EtOAc); M.p. 202-205° C.; 1H NMR (400 MHz, CDCl$_3$) 1.31 (3H, t, J=7.2 Hz), 3.56 (2H, q, J=7.2 Hz), 7.28 (1H, s), 7.32-7.37 (2H, m), 7.41-7.49 (8H, m), 7.99 (1H, s), 8.01 (1H, br), 9.28 (1H, s), 9.32 (1H, s).

Synthesis of 5,7-dichloro-4-(3,3-diphenylureido)-N-isopropylquinoline-2-carboxamide (14)

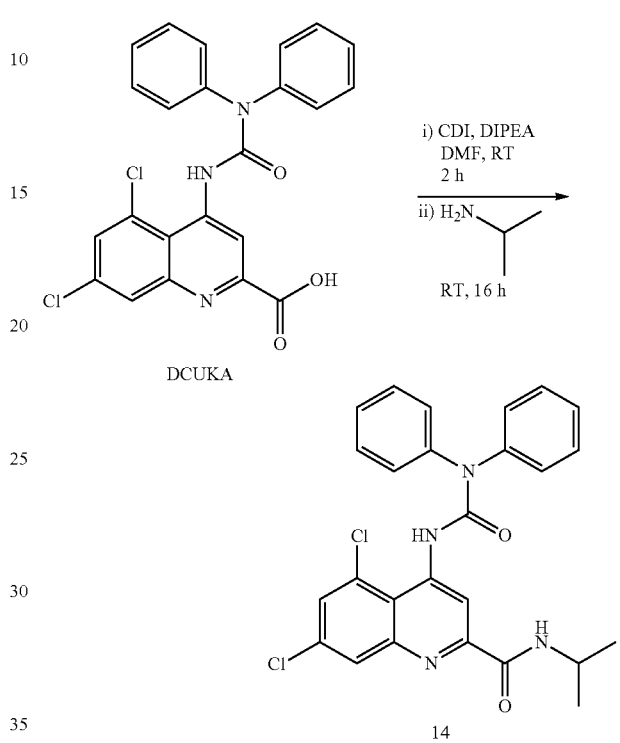

Carbonyldiimidazole (146 mg, 0.88 mmol) and diisoproylethylamine (230 uL, 1.32 mmol) were added to a solution of 5,7-dichloro-4-(3,3-diphenylureido)quinoline-2-carboxylic acid (DCUKA; 200 mg, 0.44 mmol) in dry N,N-dimethylformamide (25 mL). The reaction mixture was stirred at room temperature under nitrogen for 2 hours, before isopropylamine (110 μL, 1.32 mmol) was added. The resulting pale yellow solution was stirred at room temperature for a further 16 hours, at which point the solvent was removed under reduced pressure and the residue was dissolved in ethyl acetate (50 mL) and washed with saturated sodium hydrogen carbonate solution (2×30 mL) and 0.1M HCl (2×30 mL), followed by water (25 mL) and brine (25 mL). The organic phase was dried (MgSO$_4$) and evaporated to dryness. The target isopropylamide 14 was via silica gel chromatography (1:1 Hexanes:EtOAc) as a white solid (182 mg, 0.37 mmol, 84%). Rf 0.52 (1:1 Hexanes:EtOAc); M.p. 197-199° C.; 1H NMR (400 MHz, DMSO-d6) 1.23 (6H, d, J=6.8 Hz), 4.15 (1H, m), 7.34-7.39 (2H, m), 7.46-7.55 (8H, m), 7.76 (1H, d, J=1.9 Hz), 8.11 (1H, d, J=1.9 Hz), 8.55 (1H, d, J=8.2 Hz), 9.00 (1H, s), 9.21 (1H, s).

Example 2. Use of DCUK-OEt as a Pro-Drug for DCUKA In Vivo

This example illustrates that DCUKA is rapidly formed in vivo by ester hydrolysis after oral administration of DCUK-OEt to rats. This study was performed in accordance with the NIH Guide for the Care and Use of Laboratory Animals. A spray-dried dispersion of DCUK-OEt with the polymer HPMCAS-MG (HPMCAS-MG SDD) was prepared by Catalent Pharma. This SDD contained 15 mg of DCUK-OEt and 85 mg of the polymer per 100 mg SDD. A preparation of 0.5% hydroxypropyl methylcellulose (HPMC) was prepared by heating 100 ml of water to 60-75° C. A separate aliquot of 100 ml of water was cooled to 5° C. 500 mg of HPMC was added to 50 ml of the hot water while stirring, and then 50 ml of the cold water was added. Stirring was continued until a clear solution was formed. To make a suspension of the SDD, 15 ml of 0.5% HPMC, in aliquots, was added to a vial containing 1 g of SDD. The mixture was triturated until a uniform slurry was formed, containing 10 mg/ml of DCUK-OEt. Four rats per group were given 50 mg/kg or 100 mg/kg of DCUK-OEt in this suspension by oral gavage. Blood samples were collected from the jugular vein at 0 minutes, prior to dosing, and at 30 minutes, 60 minutes, 90 minutes, 120 minutes and 180 minutes after dosing. Blood samples were collected in NaF-containing tubes to minimize in vitro DCUK-OEt hydrolysis to DCUKA by enzymes present in rat blood.

Levels of DCUK-OEt and DCUKA were measured in whole blood samples by a validated LC-MS/MS method. Internal standards DCUKA-d10 and DCUKA-OEt-d10, were synthetically prepared (Wempe laboratory, UC Denver School of Pharmacy, Med. Chem. Core Facility). Stock 10.0 mM DMSO solutions of DCUKA, DCUKA-OEt, DCUKA-d10 and DCUKA-OEt-d100 were prepared for standard curves and internal standards, and standards and samples were diluted into 4:1 (methanol:acetonitrile, 1:1):Water (10 mM NH4OAc, 0.1% formic acid) solutions which were used to directly infuse into the mass spectrometer.

An Applied Biosystems Sciex 4000 (Applied Biosystems; Foster City, Calif.) equipped with a Shimadzu HPLC (Shimadzu Scientific Instruments, Inc.; Columbia, Md.) and Leap auto-sampler (LEAP Technologies; Carrboro, N.C.) was used. Liquid chromatography employed an Agilent Technologies, Zorbax extended-$C_{18}$ 250×4.6 mm, 5 micron column equipped with a column guard at 40° C. with a flow-rate of 0.6 mL/min. The mobile phase consisted of A: 10 mM (NH4OAc), 0.1% formic acid in H2O, and B: 50:50 ACN:MeOH. The chromatography method used was: 95% A for 2.0 min; ramped to 95% B at 7.0 min and held for 9.0 min, lastly, brought back to 95% A at 18.0 min and held for 2.0 min (20.0 min total run time). Compounds were monitored via electro-spray ionization positive ion mode (ESI+) using the following conditions: i) an ion-spray voltage of 5500 V; ii) temperature, 450° C.; iii) curtain gas (CUR; set at 10) and Collisionally Activated Dissociation (CAD; set at 12) gas were nitrogen; iv) Ion Source gas one (GS1) and two (GS2); v) entrance potential was set at 10 V; vi) quadruple one (Q1) and (Q3) were set on Unit resolution; vii) dwell time was set at 200 msec; and viii) declustering potential (DP), collision energy (CE), and collision cell exit potential (CXP) are voltages (V). Samples (10 µL) were analyzed by LC/MS-MS using the following fragmentations for quantitation: DCUKA, 452→168 m/z, $t_R$=5.3 min; DCUKA-OEt: 480→168 m/z, $t_R$=5.6 min; internal standard DCUKA-d10: 462→178 m/z; and internal standard DCUKA-OEt-d10: 490→178 m/z.

FIG. 1 graphically illustrates that DCUK-OEt can serve as a pro-drug for DCUKA after in vivo administration. Data are plotted as mean±SD values from 3-4 rats per group (data from one outlier at 60 min after the 100 mg/kg dose is not included). 50 mg/kg or 100 mg/kg of DCUK-OEt, prepared as a spray-dried dispersion formulation with the polymer HPMCAS-MG, was administered as an HPMC suspension by gavage to 4 rats per group. Blood was obtained from the jugular vein at the indicated times, and DCUKA levels were determined by LC-MS/MS analysis. The results show the blood levels of DCUKA obtained after administration of DCUK-OEt. DCUK-OEt was only detectable after the 100 mg/kg dose. The highest levels of DCUK-OEt were 0.49 µM and 0.24 µM at 60 minutes after DCUK-OEt administration, and 0.08 µM at 90 minutes after DCUK-OEt administration. Levels of DCUK-OEt were below the limit of detection in the fourth rat in the group. In contrast, as shown in FIG. 1, DCUKA levels reached approximately 3 µM after 50 mg/kg of DCUK-OEt, and approximately 11 µM after 100 mg/kg of DCUK-OEt.

Example 3. Treatment of Neuropathic Pain by DCUKA, BCUKA and DCUK-OEt

This example illustrates the ability of DCUKA, BCUKA and DCUK-OEt to reverse neuropathic pain, measured as mechanical or thermal pain, induced by cisplatin (cancer chemotherapy), Complete Freund's Adjuvant (CFA) (inflammatory pain), or diabetes (streptozotocin-induced pain) or monoiodoacetate (MIA) (osteoarthritic pain).

All studies were performed in accordance with the NIH Guide for the Care and Use of Laboratory Animals.

Drugs.

For in vivo studies of cisplatin, CFA and STZ-induced pain, DCUKA or BCUKA or DCUK-OEt, or gabapentin, were prepared in a 50% gelatin/50% canola oil emulsion (this emulsion was used as vehicle). The gelatin was prepared by adding 0.8 g of gelatin Knox, Kraft Foods North America, Tarrytown N.Y.) and 0.06 g tartaric acid (McCormick and Co., Inc., Hunt Valley, Md.) to 30 ml of purified water. The solution was heated at 98° C. for 20 minutes, then cooled to 50° C. Six ml of 95% alcohol and water were added to make 50 ml of gelatin. Various amounts of DCUKA or BCUKA or DCUK-OEt, or gabapentin, were added to 5 ml of canola oil (Safeway Inc., Pleasanton, Calif.) with stirring and sonication (VWR BIOSONIK IV, 70%) for 5 minutes, and the drug suspensions were then added to 5 ml of gelatin with stirring and sonication. The emulsions were diluted with vehicle as needed and warmed to 37° C. for oral administration to animals. Immediately prior to oral gavage, the emulsion was stirred using a vortex mixer.

For in vivo studies of MIA-induced pain, DCUKA was combined with D-α-Tocopherol polyethylene glycol 1000 succinate (TPGS 1000). DCUK-OEt (2.5 g) was weighed out into a clean glass beaker and TPGS 1000 (47.5 ml) was slowly added. The mixture was homogenized for 2-3 minutes to produce a creamy white aqueous suspension. This suspension was encapsulated into Torpac capsules (Torpac, Fairfield, N.J.) and delivered orally to rats with a Torpac capsule syringe (Wempe et al., 2012).

Four different agents were used to produce neuropathic pain. Cisplatin (Sigma-Aldrich, St. Louis, Mo.) was dissolved in 0.9% saline solution. Streptozotocin (Sigma-Aldrich) was dissolved in 20 mM sodium citrate buffer, pH=4.5. Complete Freund's Adjuvant (CFA) was obtained from Sigma-Aldrich. Sodium Mono-iodoacetate was obtained from Sigma-Aldrich and was dissolved in saline.

Measurement of Mechanical Hyperalgesia.

These studies were performed on male Sprague-Dawley rats (Taconic, Germantown Pa. or Harlan, Indianapolis Ind.) at approximately eight weeks of age. Rats were housed in an AAALAC-accredited facility with regulated lighting, temperature and humidity. Pain was tested using an electronic von Frey anesthesiometer (IITC Life Science), Woodland Hills, Calif.). Rats were placed in suspended chambers with a metal mesh floor and were allowed to acclimate for approximately 20 minutes. Mechanical stimuli were applied to the mid-plantar surface of the hind paw(s). Two different methods were used. In the first, a set of von Frey filaments with different strength ranges (g) was used, and filaments of increasing strength were applied to the paw. The force generated with each filament application was displayed on the electronic sensor. Each filament was applied five times, until a paw withdrawal response occurred ("flinch" after filament application). When a filament produced paw withdrawal in four out of five tests, or the maximal stimulus (10% of body weight) was reached, testing was stopped. The average of the four values was used to calculate the paw withdrawal threshold in g. In the second method, a semi-flexible filament was placed against the mid plantar surface of the paw with escalating pressure, until paw withdrawal was observed. The pressure (force in g) at paw withdrawal (paw withdrawal threshold) was recorded by an electronic transducer. Five measurements were taken per test, and the average value was calculated. In both methods, to avoid sensitization, a three-minute interval was imposed between measurements.

Acute Effects of DCUKA, BCUKA, DCUK-OEt and Gabapentin to Reverse Neuropathic Pain (Mechanical Hyperalgesia) Caused by Cisplatin, Complete Freund's Adjuvant (CFA), Streptozotocin (STZ) or Monoiodoacetate (MIA).

Acute Effect of DCUKA on Cisplatin-Induced Pain:

Two methods were used for cisplatin administration. 1) Cisplatin was dissolved in 0.9% saline (1 mg/ml) and injected into the tail vein in a volume of 1.5 or 2.5 ml/kg of body weight. The intravenous injection of cisplatin was followed by an injection of the same amount of saline (Joseph and Levine, 2009). The cisplatin doses were 1.5 or 2.5 mg/kg in individual experiments. 2) Cisplatin was dissolved in 0.9% saline and administered by intraperitoneal injection on days 1, 4, 8 and 12. The cisplatin doses were 2 mg/kg, 1 mg/kg, 2 mg/kg and 2 mg/kg, respectively, for a total dose of 7 mg/kg. A fresh solution of cisplatin was prepared every day before injection, and 0.9% saline (2 ml) was injected subcutaneously after the cisplatin injection (to avoid nephrotoxicity). In all experiments, rats were tested for baseline pain sensitivity (mechanical pain threshold) prior to any cisplatin treatment. The experimental designs for the studies using intravenous injections were as follows: (1) Starting at one hour after cisplatin injection, rats were given vehicle (canola oil/gelatin) orally (by intragastric gavage) twice daily (every 12 hours) for three days (these rats are controls for the study on prevention of cisplatin-induced pain, see below). On the fourth day, rats were again tested for mechanical pain threshold. On the fifth day, rats were given 50 mg/kg DCUKA or vehicle and mechanical pain threshold was tested one hour later. 2) On day 4 after cisplatin treatment, rats were given various doses of DCUKA (12.5, 25, 50, or 75 mg/kg), or vehicle, by intragastric gavage, and mechanical pain threshold was tested one hour later. 3) On day 6 after cisplatin treatment, the mechanical pain threshold was measured, and rats were given 50 mg/kg DCUKA, or vehicle, orally. The mechanical pain threshold was tested one hour later. 4) On day 6 after cisplatin treatment, rats were given various doses of DCUKA (25, 50 or 75 mg/kg) or vehicle, and one hour later, mechanical pain threshold was measured. The experimental design for experiments in which cisplatin was administered intraperitoneally were as follows: on day 14, following the cisplatin treatments (days 1, 4, 8, 12), mechanical pain threshold was tested. Rats were then given 50 mg/kg DCUKA, or vehicle, orally and the mechanical pain threshold was measured one hour later. Data are reported as the ratio of the mechanical pain threshold measured after DCUKA treatment to the baseline pre-cisplatin mechanical pain threshold (measured on the same paw).

Data Analysis of Cisplatin Experiments: Acute Effect of DCUKA and Meta-Analysis:

Depending on the experimental design, analysis consisted of either 1-way ANOVA with repeated measures or 2-way ANOVA with repeated measures (Proc Mixed, SAS v9.3, Cary, N.C.). Treatment and time are the main fixed independent effects tested. In one experiment treatment, time and the interaction between the two were assessed. The animal identification number was used as a repeated measure as there are multiple measurements on one animal, including pre and post treatment and left and right paw. All models were tested for equal variances among treatment groups (Barlett's test for homogeneity of variances) and normality (Kolmogorov-Smirnov goodness of fit test). If the data did not pass these assumptions, we adjusted accordingly in the mixed model. Some analyses used Fisher's LSD post hoc tests to compare statistical significance (p-value<0.05) between the different treatment doses and all analyses used Fisher's LSD post hoc tests to compare statistical significance between treatment group and the baseline value.

Experiments were included in the meta-analysis if they met the following requirements: 1. Mechanical pain was measured using a von Frey test, 2. Cisplatin treatment successfully induced pain (25% decrease of mechanical pain threshold) and 3. Mechanical pain was measured within 90 minutes after DCUKA administration. A mixed-model using DCUKA dose as a fixed independent variable with 5 different class levels, study identification as both a random and a repeated measure and rat identification as a random effect was used to determine the overall effectiveness of DCUKA on neuropathic pain (Proc Mixed, SAS v9.3, Cory, N.C.). Fisher's LSD post hoc tests were used for pairwise comparisons of the DCUKA doses.

Comparison of the Effects of DCUKA, BCUKA and Gabapentin on Cisplatin-Induced Pain.

Cisplatin was administered intraperitoneally on days 1 (2 mg/kg), 4 (1 mg/kg), 8 (2 mg/kg) and 12 (2 mg/kg) (7 mg/kg total dose). Cisplatin was prepared daily and 2 ml of 0.9% saline was administered subcutaneously after each cisplatin injection. On day 14, the mechanical pain threshold was measured, and rats received vehicle (canola oil/gelatin), DCUKA (50 mg/kg), BCUKA (50 mg/kg) or gabapentin (30 mg/kg, a dose equimolar to DCUKA and BCUKA). One and two hours later, the mechanical pain threshold was again tested. Data are reported as the ratio of the mechanical pain threshold measured after DCUKA, BCUKA or gabapentin treatment to the baseline mechanical pain threshold (measured on the same paw). Statistical analysis was a 2-way ANOVA with repeated measures (Proc Mixed, SAS v9.3). Treatment and time were the main fixed independent effects, and the interaction was also tested. The animal identification number was used as a repeated measure. Fisher's LSD post hoc tests were used to compare significance (p<0.05) between the different times within treatment groups.

Acute Effect of DCUKA on Complete Freund's Adjuvant (CFA)-Induced Neuropathic Pain.

After measurement of the baseline paw withdrawal threshold, CFA (0.1 ml) was administered subcutaneously into the plantar surface of the left hind paw of the rat under light isoflurane anesthesia (5% for induction and 2% for maintenance). Rats were left in their home cage for 48 hours. Paper bedding was used to avoid pressure neuropathies caused by hard bedding. At 48 or 60 hours after CFA injection, rats were given vehicle (canola oil/gelatin) orally, or various doses of DCUKA orally, by intragastric gavage, and the mechanical pain threshold was determined one hour later. Data are presented as the ratio of the mechanical pain threshold measured after DCUKA treatment to the baseline mechanical pain threshold.

Data Analysis of CFA Experiments: Acute Effect of 50 mg/kg DCUKA and Meta-Analysis of DCUKA Dose-Response.

Each experiment was analyzed with a 1-way ANOVA (Proc Glm or Proc Mixed, SAS v9.3, Cary, N.C.). Treatment group was the fixed independent effect tested. All models were tested for equal variances among treatment groups (Barlett's test for homogeneity of variances) and normality (Kolmogorov-Smirnov goodness of fit test). If the data did not pass these assumptions, a mixed model was used. All analyses used Fisher's LSD post hoc tests to compare statistical significance (p-value<0.05) among the different treatment groups.

Comparison of the Effect of DCUKA and BCUKA on CFA-Induced Neuropathic Pain.

The baseline mechanical pain threshold was determined, and animals were treated with CFA as described above. At 48 hours after CFA treatment, rats were given vehicle (canola oil/gelatin) (n=17), 50 mg/kg DCUKA (n=17) or 50 mg/kg BCUKA (n=6). The mechanical pain threshold was tested one hour later, and data are reported as the ratio of the pain threshold after vehicle, DCUKA or BCUKA treatment to the baseline pain threshold, measured on the same paw. A one-way ANOVA followed by Fisher's LSD post hoc test was used to determine statistical significance (p<0.05).

Acute Effect of DCUKA on Streptozotocin (STZ)-Nduced Neuropathic Pain (Model of Diabetic Neuropathic Pain).

After measurement of the baseline paw withdrawal threshold, baseline body weight and blood glucose concentrations were determined (blood glucose measured on tail blood, using the ASCENSIA CONTOUR Blood Glucose Monitoring System, Bayer, Pittsburgh, Pa.). Rats were fasted overnight and injected intraperitoneally with vehicle (20 mM sodium citrate, pH 4.5, Sigma-Aldrich), or 50 mg/kg STZ in vehicle. The STZ solution was prepared each day and used within 10 minutes. Food was given to the rats 30 minutes after STZ treatment. Three days after STZ treatment, blood glucose levels were again measured, and rats with a blood glucose level above 350 mg/dl were considered "diabetic". If the blood glucose level was below 350 mg/dl, the rat was given a second dose of STZ (45 mg/kg), using the same procedure. Fourteen days after the first STZ treatment, rats were given vehicle (canola oil/gelatin) or various doses of DCUKA orally, and the mechanical pain threshold was tested at various times after these treatments. Data are presented as the ratio of the mechanical pain threshold following DCUKA treatment to the baseline mechanical pain threshold (measured on the same paw).

Individual Experimental Analysis.

Data points were considered as outliers and removed from the dataset if the ratio of the mechanical pain threshold to baseline was outside the corresponding treatment group mean±2 standard deviations. Each experiment was analyzed with a 1-way ANOVA (Proc Glm or Proc Mixed, SAS v9.3, Cary, N.C.). Treatment group was the fixed independent effect tested. All models were tested for equal variances among treatment groups (Barlett's test for homogeneity of variances) and normality (Kolmogorov-Smirnov goodness of fit test). If the data did not pass these assumptions, a mixed model was used. All analyses used Fisher's LSD post hoc tests to compare statistical significance (p-value<0.05) between the different treatments.

Acute Effect of DCUKA on Monoiodoacetate (MIA)-Induced Neuropathic Pain (Model of Osteoarthritic Neuropathic Pain).

Rats were anesthetized with isoflurane and right knees were shaved and injected with vehicle or with MIA, to induce disease. Animals were weighed weekly until pain measurements were made on day 20. Baseline paw withdrawal measurements were made in animals not treated with MIA. On day 21 groups of animals were dosed orally with vehicle or DCUKA (1 or 2 capsule p.o.; doses approximately 50 mg/kg or 100 mg/kg). The mechanical pain threshold was tested at 90 minutes after drug administration. At the end of testing, blood was taken from the tail vein for determination of DCUKA levels by LC-MS/MS analysis. Data are presented as the ratio of the mechanical pain threshold following DCUKA treatment to the mechanical pain threshold determined in animals with no drug or MIA treatment.

Data Analysis of MIA Experiments.

The experiment was analyzed with a 1-way ANOVA (Sigma Plot 12) and used the Holm-Sidak post hoc tests for all pairwise comparisons. P values <0.05 were considered statistically significant. Given that administration of 1 capsule of DCUKA did not significantly affect the mechanical pain threshold (FIG. 8), the blood levels of Kindolor after this treatment were assessed. It was determined that blood levels of Kindolor <500 ng/ml (<1.1 µM) were obtained following administration of a single capsule, and this blood level was deemed ineffective in treating MIA-induced neuropathic pain.

Figure 2:
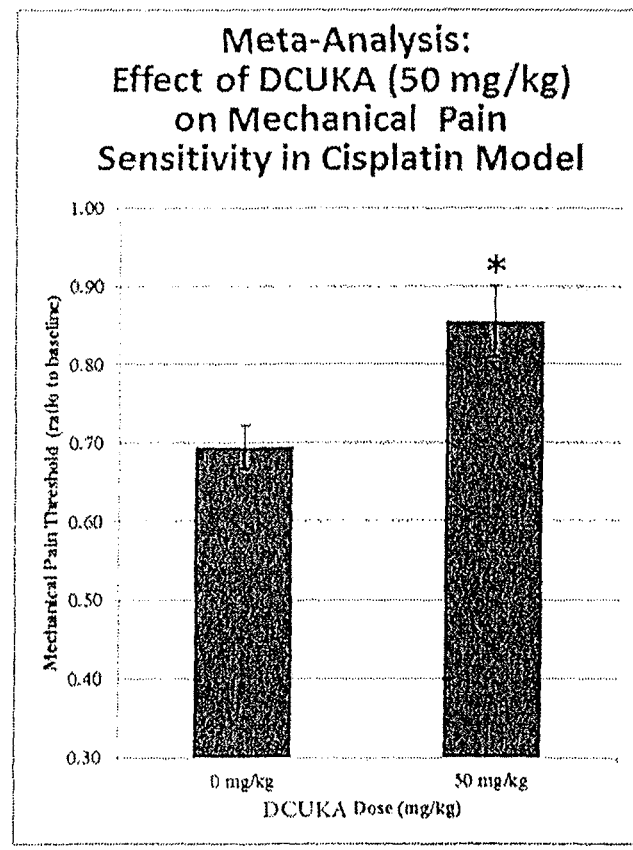
FIG. 2 graphically illustrates the treatment of cisplatin-induced neuropathic pain by DCUKA (50 mg/kg). In rats treated with the cancer chemotherapy agent, cisplatin, the cisplatin treatment reduces the mechanical pain threshold and DCUKA treatment reverses this effect and increases the mechanical pain threshold toward control levels. The data show the ratio of the mechanical pain threshold after cisplatin or cisplatin plus DCUKA treatment to the pre-cisplatin treatment mechanical pain threshold.

FIG. 2 illustrates that DCUKA (50 mg/kg) treatment reverses neuropathic pain caused by treatment of rats with the cancer chemotherapeutic agent, cisplatin. Combined results from six experiments are shown. Treatment means±1 SEM plotted. *P-value <0.0001 compared to control (0 mg/kg DCUKA). In all experiments, rats were tested for baseline mechanical pain threshold prior to cisplatin treatment. Following cisplatin treatments described earlier, rats were given DCUKA, and one hour later, the mechanical pain threshold was again determined. The results show the ratio of the mechanical pain threshold measured at one hour after vehicle or DCUKA administration compared to the baseline (pre-cisplatin treatment) mechanical pain threshold.

Figure 3:
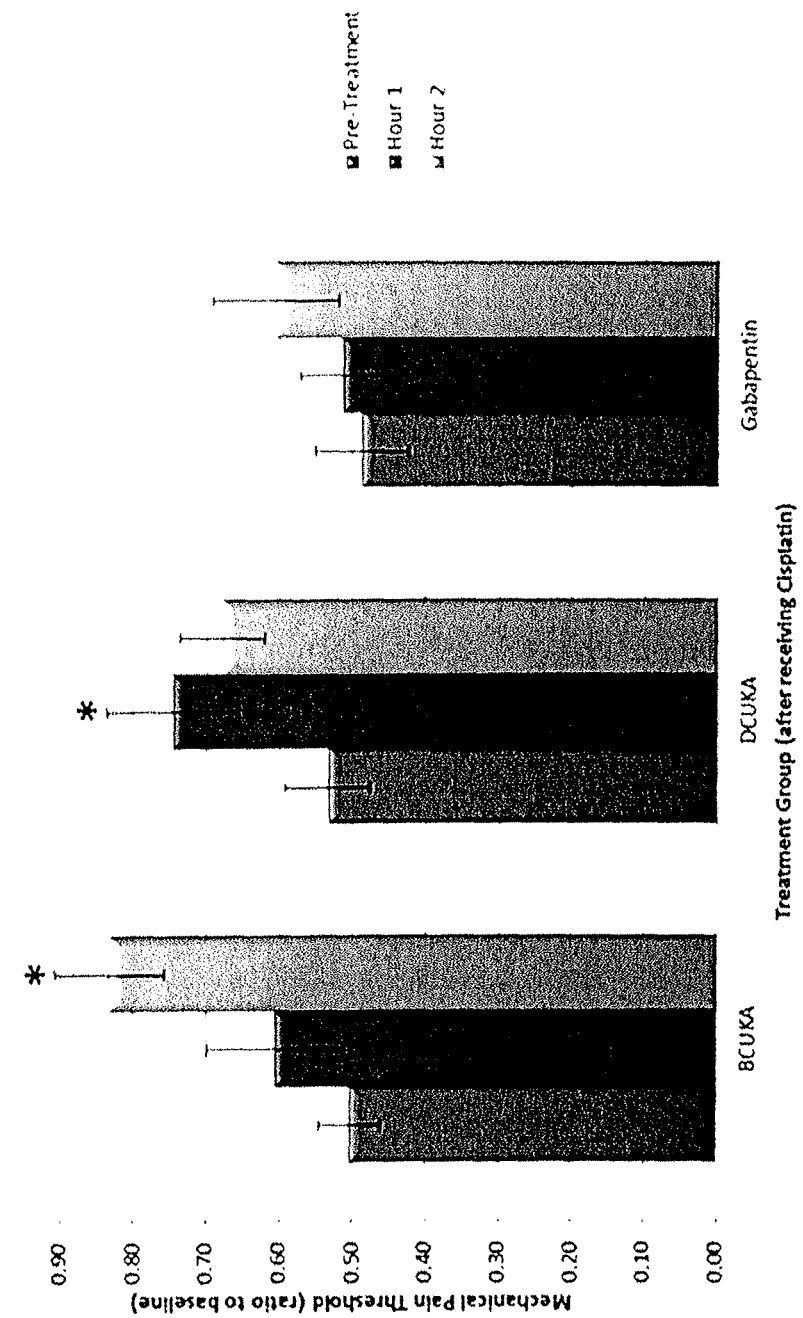
FIG. 3 graphically illustrates a comparison of the effects of equimolar doses of DCUKA, BCUKA and gabapentin to reverse cisplatin-induced neuropathic pain, measured by changes in the mechanical pain threshold.

FIG. 3 graphically compares the effect of DCUKA (50 mg/kg), BCUKA (50 mg/kg) and gabapentin (Neurontin, 30 mg/kg) on neuropathic pain induced by the chemotherapeutic agent, cisplatin. The mean mechanical pain threshold±1 standard error is plotted for each treatment group and time. *P<0.05 compared to the corresponding pre-treatment group. Rats were tested for baseline mechanical pain threshold prior to cisplatin treatment, and were treated with cisplatin as described earlier. Following cisplatin treatment the mechanical pain threshold was measured, and rats were given oral doses of vehicle, DCUKA, BCUKA, or gabapentin. The mechanical pain threshold was again measured at 1 and 2 hours after these treatments. Data are the ratio of the mechanical pain threshold measured prior to DCUKA, BCUKA or gabapentin administration, and 1 and 2 hours later. Cisplatin treatment alone ("pretreatment") significantly reduced the mechanical pain threshold, compared to baseline, and DCUKA and BCUKA significantly reversed the drop in mechanical pain threshold. Gabapentin, at a dose equimolar to DCUKA and BCUKA, did not significantly reverse the cisplatin-induced decrease in the mechanical pain threshold.

Figure 4:
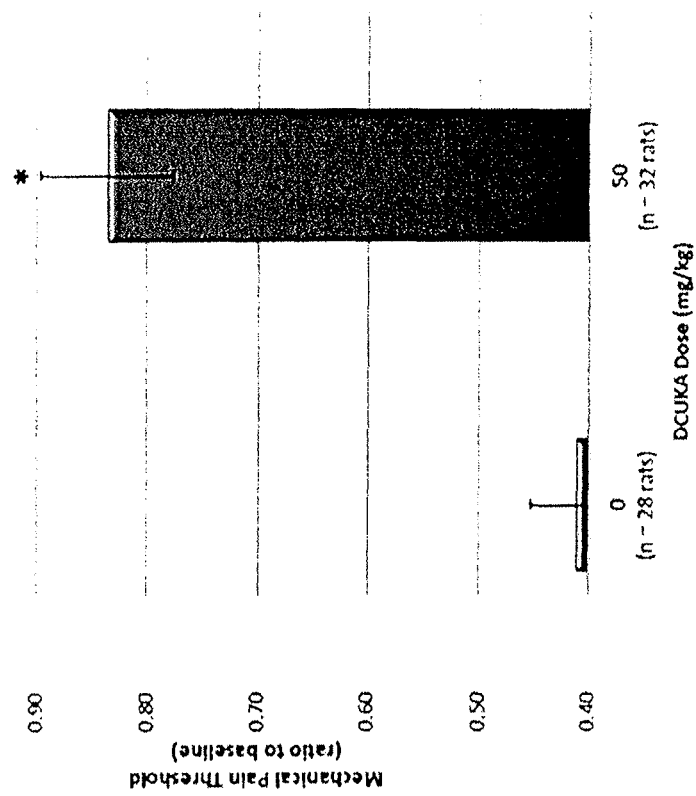
FIG. 4 graphically illustrates the reversal by DCUKA (50 mg/kg) of neuropathic pain induced by treatment of rats with Complete Freund's Adjuvant (CFA). CFA treatment of the rat's paw induces inflammation and reduces the mechanical pain threshold. DCUKA treatment reverses the reduction in the mechanical pain threshold in CFA-treated rats and returns the threshold toward the baseline level. The data show the ratio of the mechanical pain threshold after CFA or CFA plus DCUKA treatment to the mechanical pain threshold prior to CFA treatment.

FIG. 4 graphically illustrates that DCUKA treats the neuropathic pain induced by treatment of rats with Complete Freund's Adjuvant (CFA) to produce an inflammatory response. Data are combined from three experiments. In each experiment, the baseline mechanical pain threshold (force, in g, causing paw withdrawal) was first measured using an electronic von Frey anesthesiometer. Rats were then injected with 0.1 ml complete Freund's Adjuvant (CFA) into the plantar surface of the left hind paw. Forty-eight to 60 hours later, when CFA-induced pain had developed, rats received oral administration of vehicle (gelatin/canola oil emulsion) or 50 mg/kg DCUKA. One hour later, mechanical pain threshold was again measured. The results show the ratio of mechanical pain threshold measured one hour after vehicle or DCUKA treatment to the baseline mechanical pain threshold. A post hoc Fisher's LSD t-test for pairwise comparisons showed a significant (*) difference between 50 mg/kg DCUKA and 0 mg/kg DCUKA (p-value <0.0001). CFA treatment reduced the mechanical pain threshold by approximately 60%, and DCUKA treatment reversed this effect and increased the mechanical pain threshold in the CFA-treated paw to a level not significantly different from the baseline level.

Figure 5:
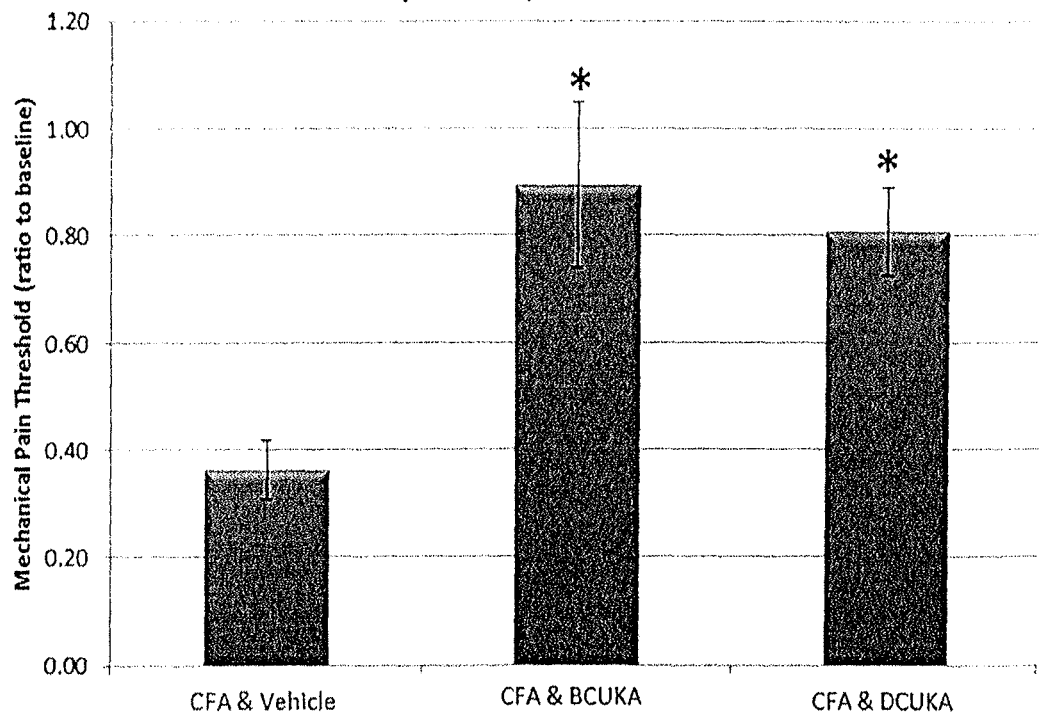
FIG. 5 illustrates a comparison of the effect of DCUKA (50 mg/kg) and BCUKA (50 mg/kg) to reverse neuropathic pain induced by treatment of rats with CFA. The data show the ratio of the mechanical pain threshold after CFA treatment, or CFA plus DCUKA or BCUKA treatment, to the baseline (pre-CFA) mechanical pain threshold.

FIG. 5 graphically illustrates a comparison of the effect of DCUKA (50 mg/kg) and BCUKA (50 mg/kg) to treat neuropathic pain produced by CFA treatment. Mechanical pain threshold for each animal is represented by the ratio to baseline for the injected paw only. The mean mechanical pain threshold±1 standard error is plotted for each treatment group. *P<0.05 compared to vehicle. Baseline mechanical pain threshold was measured, and rats were treated with CFA as described earlier. Forty-eight hours later, rats were given vehicle (canola oil/gelatin), DCUKA or BCUKA, and one hour later the mechanical pain threshold was measured. CFA treatment reduced the mechanical pain threshold to about 40% of baseline, and treatment with DCUKA (n=17) or BCUKA (n=6) reversed the mechanical pain threshold to a level not significantly different from baseline.

The dose dependence of the effects of DCUKA on neuropathic pain produced by CFA was determined using a meta-analysis approach. The results are shown in FIG. 6. Mechanical pain threshold for each animal is represented by the ratio to baseline for the injected paw only. The mean mechanical pain threshold±1 standard error is plotted for each treatment group. This is based on treatment means from the 5 studies included in the meta analysis. *P<0.05 compared to the vehicle (0 mg/kg) treatment group. In all experiments with CFA, the baseline mechanical pain threshold was measured with an electronic von Frey anesthesiometer. CFA was injected into the plantar surface of the left hind paw and, at 48 hours after injection, rats were given oral vehicle (gelatin/canola oil) or DCUKA. The mechanical pain threshold was again measured at 60 min after vehicle or DCUKA administration. For an experiment to be included in the meta-analysis, the requirements were: 1) CFA treatment produced at least a 25% decrease in the mechanical pain threshold; 2) the pain threshold was measured at 60 min after DCUKA or vehicle administration. Five experiments, in which different doses of DCUKA were tested, met these requirements. The mechanical pain threshold, as a ratio to the baseline mechanical pain threshold, is shown as mean±SEM. There was a significant overall effect of DCUKA (F(5,125)=7.71, P<0.0001). CFA treatment reduced the mechanical pain threshold by approximately 60%, and this effect was significantly reversed by DCUKA doses of 30 mg/kg and higher, i.e., the pain threshold returned to the baseline level.

FIG. 7 illustrates that DCUKA reverses the neuropathic pain that accompanies diabetes. Diabetes was induced in rats by injection of streptozotocin (STZ) as described earlier. A post hoc Fisher's LSD t-test for pairwise comparisons, showed a significant (*) difference between 50 mg/kg DCUKA and 0 mg/kg DCUKA (difference=0.60, p-value <0.0001). Combined data from three experiments are shown. In each experiment, baseline mechanical pain threshold was tested using an electronic von Frey anesthesiometer. Fourteen days after STZ treatment, vehicle (gelatin/canola oil) or 40 or 50 mg/kg DCUKA (these doses did not have significantly different effects) was administered orally and mechanical pain was assessed 90 minutes later. The results show the ratio of the mechanical pain threshold following vehicle/DCUKA treatment to the baseline mechanical pain threshold. STZ reduced the mechanical pain threshold by approximately 40%, and this effect was reversed to the baseline level by DCUKA treatment.

The dose-dependence of the effects of DCUKA on STZ-induced neuropathic pain was determined by a meta-analysis approach. Requirements for an experiment to be included in the meta-analysis were: 1) STZ treatment induced neuropathic pain, as measured by a decrease in mechanical pain threshold of at least 25%; 2) pain was measured 90 minutes after vehicle or DCUKA treatment. Four experiments that met these criteria were included in the meta-analysis.

FIG. 8 shows the dose-dependence of the effect of DCUKA to treat STZ-induced neuropathic pain. The data are reported as the ratio of the mechanical pain threshold after vehicle or DCUKA treatment to the baseline pain threshold measured on the same paw. *P<0.05 compared to the vehicle treatment group. There was an overall significant effect of DCUKA on mechanical pain threshold (F(7, 115)=8.48, p<0.0001). STZ treatment induced approximately a 40% reduction in the pain threshold, and doses of DCUKA of 30 mg/kg and higher reversed the effect of STZ and increased the pain threshold back to the baseline level.

FIG. 9 shows the dose-dependence of DCUKA to treat MIA-induced neuropathic pain. The data are reported as the mean±SEM ratio of the mechanical pain threshold after vehicle (0 capsules) or DCUKA treatment (1 or 2 capsules), to the baseline pain threshold measured in animals not treated with MIA or drugs. *P<0.05 compared to the vehicle group (ANOVA and post hoc comparisons). There was an overall significant effect of DCUKA on mechanical pain threshold (F(2,26)=4.07, p=0.029). MIA treatment produced approximately a 60% reduction in the pain threshold, and a dose of approximately 100 mg/kg of DCUKA (2 capsules) significantly reversed the effect of MIA.

Example 4 DCUKA and DCUK-OEt Enhance the Effect of Morphine on CFA-Induced Neuropathic Pain The data below demonstrate that low doses of DCUKA together with morphine result in a synergistic effect on reduction of mechanical allodynic and thermal hyperalgesic pain produced by an inflammatory agent.

CFA treatment and measurement of mechanical pain threshold are described under Example 3. In this experiment, mechanical pain threshold was tested at baseline. At 48 hours after CFA treatment, vehicle, DCUKA or morphine, or the combination of DCUKA and morphine, were injected 30 minutes prior to measurement of the mechanical pain threshold.

Thermal Hypersensitivity Test (Radiant Heat Paw Withdrawal Test).

Rats were placed in clear plastic chambers on a glass surface and were habituated for 15 minutes before testing. Thermal sensitivity was measured by using paw withdrawal latency to a radiant heat stimulus. A radiant heat source (i.e., infrared) was activated with a timer and focused onto the plantar surface of the left hind paw. A motion detector that halted both lamp and timer when the paw was withdrawn determined paw withdrawal latency. The latencies were measured before and after drug or vehicle administration. A maximum cutoff of 33 seconds was used to prevent tissue damage. In this experiment, rats were injected with DCUK-OEt, immediately followed by morphine at increasing dose ratios, and tested 30 minutes later.

FIG. 10A demonstrates that combining doses of DCUKA and morphine that in themselves, are ineffective in producing analgesia, results in a complete reversal of inflammation-induced chronic pain. These data are consistent with the conclusion that the combination of DCUKA and morphine has a greater effect than the additive effects of each drug alone, as determined by each of the "Effect-Based Strategy" approaches discussed by Foucquier & Guedj (2015). This figure illustrates the "Combination Subthreshold" approach, where the combination of ineffective doses of drugs yields a significant effect. FIGS. 10B and 10C provide evidence that the combination of DCUK-OEt and morphine provides a supra-additive effect, as compared to either agent given alone. In this case, thermal hyperalgesia produced by CFA treatment was tested. The $ED_{50}$ for the anti-hyperalgesic response to morphine was significantly reduced by administering DCUK-OEt in a dose ratio to morphine of >30:1. For instance, a dose of 0.2 mg/kg morphine produces approximately a 20% antihyperalgesic response. Combined with 6.4 mg of DCUK-OEt, the response is increased to 40%. DCUK-OEt decreased the ED50 for the anti-hyperalgesic actions of morphine at 18:1(†P<0.7) and 32:1 (*P<0.05), DCUK-OEt/morphine dose ratios compared to Morphine alone by one-way ANOVA with post hoc Dunnett's test.

Example 5 DCUKA Enhances the Effect of Oxycodone and Methadone to Treat FA-Induced Neuropathic Pain The data below demonstrate that low doses of DCUKA potentiate the effect of low doses of oxycodone or methadone to reduce mechanical allodynia produced by an inflammatory agent. Data are presented as the mean±SEM ratio of the mechanical pain threshold in the treated paw after drug or vehicle (VEH) treatment to the mechanical pain threshold prior to treatment with Freund's adjuvant (FA). *P<0.05 compared to the vehicle-treated group (n=8/group, ANOVA and post hoc comparisons).

After baseline mechanical pain testing, rats were injected into the right hind paw with a mixture of Incomplete Freund's Adjuvant (FA) and *Mycobacterium butyricum* (similar to Complete Freund's Adjuvant). 72 hours later, mechanical pain testing was repeated, using a modified version of the Von Frey testing procedure described in Example 3. Rats were tested using a set of von Frey hairs ranging from 3.16 to 5.18 absolute threshold. Each hair was applied three times, to determine which stiffness hair the rat will respond to 100% of the time. Data were analyzed by the Psychofit program. On day 4, to determine responses to individual drugs, groups of rats were given vehicle or doses of DCUKA (one or two capsules, p.o., as described in Example 3) or doses of oxycodone (0.1, 0.25 or 1 mg/kg ip) or doses of methadone (1.5, 2.5 or 3.5 mg/kg ip), and von Frey testing was performed 75-90 minutes after dosing. On day 8, the effect of the combination of low doses (one capsule) of DCUKA with low doses of oxycodone or methadone was assessed. Rats were given DCUKA plus vehicle, oxycodone plus vehicle, methadone plus vehicle, or DCUKA plus oxycodone or DCUKA plus methadone, using doses determined from the initial phase of the study. FIG. 11 demonstrates that combining doses of DCUKA (1 capsule) and oxycodone (0.1 mg/kg) that are in themselves ineffective in producing antihyperalgesia, results in a reduction of inflammation-induced chronic pain. These data are consistent with the conclusion that the combination of DCUKA and oxycodone has a greater effect than the additive effects of each drug alone, as determined by all four of the "Effect-Based Strategy" approaches discussed by Foucquier and Guedj (2015). This figure illustrates the "Combination Subthreshold" approach, i.e., the combination of non-effective doses of drugs yields a significant effect. The solid line indicates the baseline mechanical pain threshold ratio in animals treated with Freund's adjuvant and vehicle. The increase above this line indicates the (non-significant) effects of DCUKA or oxycodone alone. The interrupted dotted line indicates the expected additive effect of the drug combination. The increased effect of the drug combination (i.e., DCUKA plus oxycodone 0.1 mg/kg) above the interrupted dotted line, indicates a "positive combination effect" (Foucquier and Guedj, 2015).

FIG. 12 demonstrates that DCUKA (1 capsule) potentiates the effect of methadone (1.5 or 3.5 mg/kg) to reduce inflammation-induced chronic pain. Data are presented as the mean±SEM ratio of the mechanical pain threshold in the treated paw after drug or vehicle (VEH) treatment, to the mechanical pain threshold prior to treatment with Freund's adjuvant (FA). *P<0.05 compared to DCUKA/VEH or methadone 1.5 mg/kg alone; **P<0.05 compared to DCUKA/VEH or methadone 3.5 mg/kg alone; +P<0.05 compared to VEH (n=8/group, ANOVA and post hoc comparisons).

These data are consistent with the conclusion that the combination of DCUKA and methadone has a greater effect than the additive effects of each drug alone, as determined by each of the "Effect-Based Strategy" approaches discussed by Foucquier and Guedj (2015). For 1.5 mg/kg methadone, this figure illustrates the "Combination Subthreshold" approach, in which the combination of ineffective doses of drugs yields a significant effect. The solid black line indicates the baseline mechanical pain threshold ratio in animals treated with Freund's adjuvant and vehicle. The increase above this line reflects the (non-significant) effects of DCUKA or methadone (1.5 mg/kg) alone. The gray line indicates the expected additive effect of the combination of DCUKA and 1.5 mg/kg methadone. The increased effect of the combination of DCUKA and methadone 1.5 mg/kg reflects a "positive combination effect" (Foucquier and Guedj, 2015). For 3.5 mg/kg methadone, the figure illustrates the "Highest Single Agent" approach, which reflects the fact that the effect of the drug combination is greater than the effects produced by its individual components. The interrupted dotted line indicates the expected additive effects of 3.5 mg/kg methadone and DCUKA. The increased effect of the drug combination above this line reflects a "positive combination effect." (Foucquier and Guedj, 2015).

Example 6 DCUKA Enhances the Effect of Tramadol to Treat MIA-Induced Neuropathic Pain The data below demonstrate that in another model of chronic pain, the MIA osteoarthritic model that low doses of DCUKA can synergize with a low dose of another narcotic analgesic (tramadol) to reduce hyperalgesia. Tramadol acts at the μ opiate receptor and is also a serotonin and norepinephrine reuptake inhibitor.

After administration of MIA as described in Example 3, rats were initially tested for the acute effect of different doses of DCUKA at 21 days after MIA treatment, with results shown in FIG. 13. The administration of a single capsule of DCUKA (approximately 50 mg/kg) did not significantly affect MIA-induced pain. Blood levels of DCUKA at 2-2.5 hours after dosing were determined to be <500 ng/ml (<1.1 μM) at this time. This blood level of DCUKA was considered to be ineffective in reducing MIA-induced neuropathic pain. Rats were again tested for mechanical pain threshold at 29 days after treatment with MIA (pain threshold was re-assessed on day 28 to determine that there was no significant difference from the initial test on day 20). Rats were given vehicle, 1 capsule (low dose) of DCUKA p.o., 5 mg/kg (low dose) p.o. tramadol or 1 capsule of DCUKA plus 5 mg/kg tramadol, 90 minutes prior to measurement of mechanical pain threshold, as described in Example 3, and blood was obtained from the jugular vein after testing for assessment of DCUKA levels by LC-MS/MS methods described in Example 2.

Data Analysis.

Data are presented as the ratio of the mechanical pain threshold after drug treatment, to the non-MIA, non-drug treated baseline mechanical pain threshold. Data from two outliers in the DCUKA plus tramadol group were eliminated from the analysis. Animals with a blood level of DCUKA <500 ng/ml, the level that had previously been found to be ineffective in reversing MIA-induced neuropathic pain, were deemed to have received a "low dose" of DCUKA. Data from these animals was used for analysis of differences among groups by 1-way ANOVA and the Holm-Sidak test for all pairwise comparisons.

FIG. 13 demonstrates that doses of DCUKA (1 capsule, where the blood level of DCUKA was <500 ng/ml) and tramadol (5 mg/kg), which by themselves do not have a significant effect on mechanical pain threshold compared to vehicle, when combined, produce a significant reversal of the reduction of the pain threshold caused by MIA treatment. Data are presented as mean±SEM of the ratio of mechanical pain threshold after treatment with low-dose DCUKA, low-dose (5 mg/kg) tramadol, or the combination of low dose DCUKA and low dose tramadol, to the pre-MIA treatment mechanical pain threshold. *P<0.05 compared to all other groups (ANOVA and post hoc comparisons).

These data are consistent with the conclusion that the combination of DCUKA and tramadol has a greater effect than the additive effects of each drug alone, as determined by each of the "Effect-Based Strategy" approaches discussed by Foucquier and Guedj (2015). This figure illustrates the "Highest Single Agent" approach, which reflects the fact that the effect of the drug combination is greater than the effect produced by its individual components. The solid line indicates the baseline mechanical pain threshold ratio in animals treated with MIA and vehicle. The (non-significant) effect of tramadol is indicated by the increase over the baseline, and this increase is indicated by the interrupted dotted line. The effect of the drug combination above the interrupted dotted line reflects a "positive combination effect" (Foucquier and Guedj (2015).

Example 7 DCUKA Enhances the Effect of Aspirin to Treat STZ-Induced Neuropathic Pain The data below demonstrate that in another model of chronic pain, the STZ diabetic neuropathy model, DCUKA can synergize with another analgesic (aspirin) to reduce allodynia.

After administration of streptozotocin (STZ) as described in Example 3, rats were tested for allodynia using a von Frey apparatus. Sixty minutes prior to testing, rats were divided into four groups. Group 1 received vehicle; Group 2 received DCUKA; Group 3 received aspirin; and Group 4 received a combination of DCUKA and aspirin.

Figure 14:
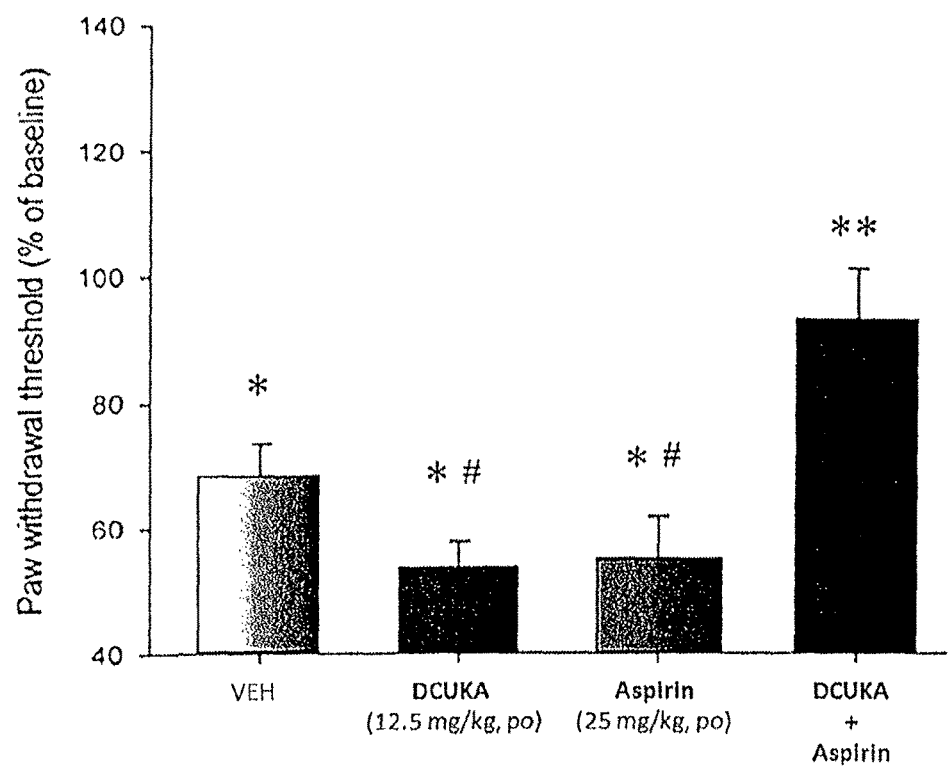
FIG. 14 illustrates that DCUKA potentiates the ability of aspirin to reverse STZ-induced neuropathic pain (diabetic neuropathy).

FIG. 14 demonstrates that doses of DCUKA (12.5 mg/kg) or aspirin (25 mg/kg) which by themselves do not have any significant effect on allodynia, when combined, completely reverse the hyper-responsiveness, i.e., return the pain threshold to the baseline level. These data are consistent with the conclusion that the combination of DCUKA and aspirin has a greater effect than the additive effects of each drug alone, as determined by each of the "Effect-Based Strategy" approaches discussed by Foucquier & Guedj (2015). This figure illustrates the "Combination Subthreshold" approach where the combination of ineffective doses of drugs yields a significant effect.

Example 8 DCUKA Potentiates the Effect of Diclofenac to Treat FA-Induced Neuropathic Pain The data below demonstrate that a low dose of DCUKA (one capsule, as described in Example 1) potentiates the effect of a low dose of diclofenac to reduce mechanical allodynia produced by an inflammatory agent. Data are presented as the mean±SEM ratio of the mechanical pain threshold in the treated paw after drug or vehicle (VEH) treatment, to the mechanical pain threshold prior to treatment with Freund's adjuvant (FA). *P<0.05 compared to DCUKA or Diclofenac 1.5 mg/kg alone; **P<0.05 compared to DCUKA, or Diclofenac 10 mg/kg alone (ANOVA and post hoc comparisons).

Figure 15:
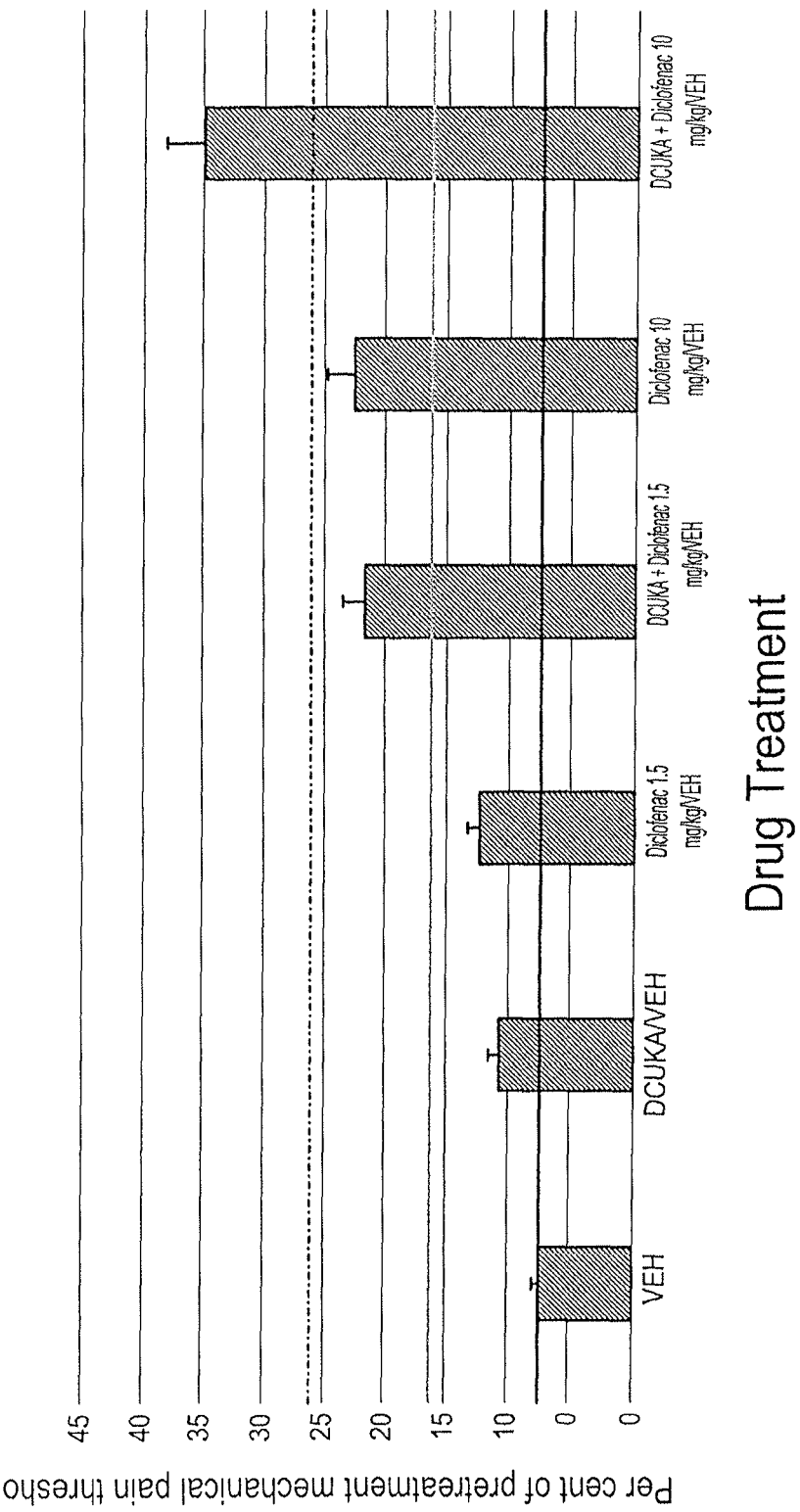
FIG. 15 illustrates that DCUKA potentiates the ability of diclofenac to reverse CFA-induced neuropathic pain.

Rats were treated with Freund's adjuvant and tested for mechanical pain as described in Examples 2 and 5. Groups of rats were given different doses of diclofenac on day 4 to determine appropriate doses for the experiment testing the combined effects of DCUKA and diclofenac. Different groups of rats were tested on day 4 after administration of a single capsule of DCUKA or low doses of diclofenac alone and in combination. FIG. 15 shows that DCUKA potentiates the effect of diclofenac to reduce inflammation-induced chronic pain. These data are consistent with the conclusion that the combination of DCUKA and Diclofenac has a greater effect than the additive effects of each drug alone, as determined by each of the "Effect-Based Strategy" approaches discussed by Foucquier and Guedj (2015). For Diclofenac 1.5 mg/kg, this figure illustrates the "Combination Subthreshold" approach, in which the combination of ineffective doses of drugs yields a significant effect. The solid black line indicates the baseline mechanical pain threshold ratio in animals treated with Freund's adjuvant and vehicle. The increase above this line indicates the (non-significant) effect of DCUKA or Diclofenac 1.5 mg/kg alone. The gray line indicates the expected additive effect of DCUKA and Diclofenac 1.5 mg/kg. The increased effect of the combination of DCUKA and Diclofenac 1.5 mg/kg, above the gray line, indicates a "positive combination effect." For 10 mg/kg Diclofenac, the figure illustrates the "Highest Single Agent" approach, which reflects the fact that the effect of the drugs in combination is greater than the effects produced by the individual components. The interrupted dotted line indicates the expected additive effects of DCUKA and Diclofenac 10 mg/kg. The increased effect of the drug combination, above the interrupted dotted line, indicates a "positive combination effect" (Foucquier and Guedj, 2015).

Example 9 Prevention of Cisplatin- and CFA-Induced Neuropathic Pain by DCUKA

The data below show that treatment of animals with DCUKA following insult, but prior to development of neuropathic pain, can prevent the development of the pain. Rats were treated with cisplatin or CFA, and mechanical pain threshold was measured, as described under Example 3.

Prevention of CFA-Induced Neuropathic Pain by DCUKA.

After baseline measurement of the mechanical pain threshold, rats were treated with CFA as described earlier. Following the CFA injection, rats were given vehicle (canola oil/gelatin) (n=7) or 50 mg/kg DCUKA (n=7) orally by intragastric gavage. Rats then received three more treatments with vehicle or DCUKA at 12-hour intervals. At 60 hours after CFA treatment, the mechanical pain threshold was again tested.

Prevention of Cisplatin-Induced Neuropathic Pain by DCUKA.

One day after baseline measurement of the mechanical pain threshold, rats were injected i.p. with cisplatin. Cisplatin injections were again given on days 4, 8, and 12. Starting one hour after the first cisplatin injection, rats were given 50 mg/kg DCUKA or vehicle via intragastric gavage twice daily for 14 days. After the last treatment (day 15) the mechanical pain threshold was again tested. The pain threshold was then tested once weekly for 4 weeks, with no further treatments.

Figure 16:
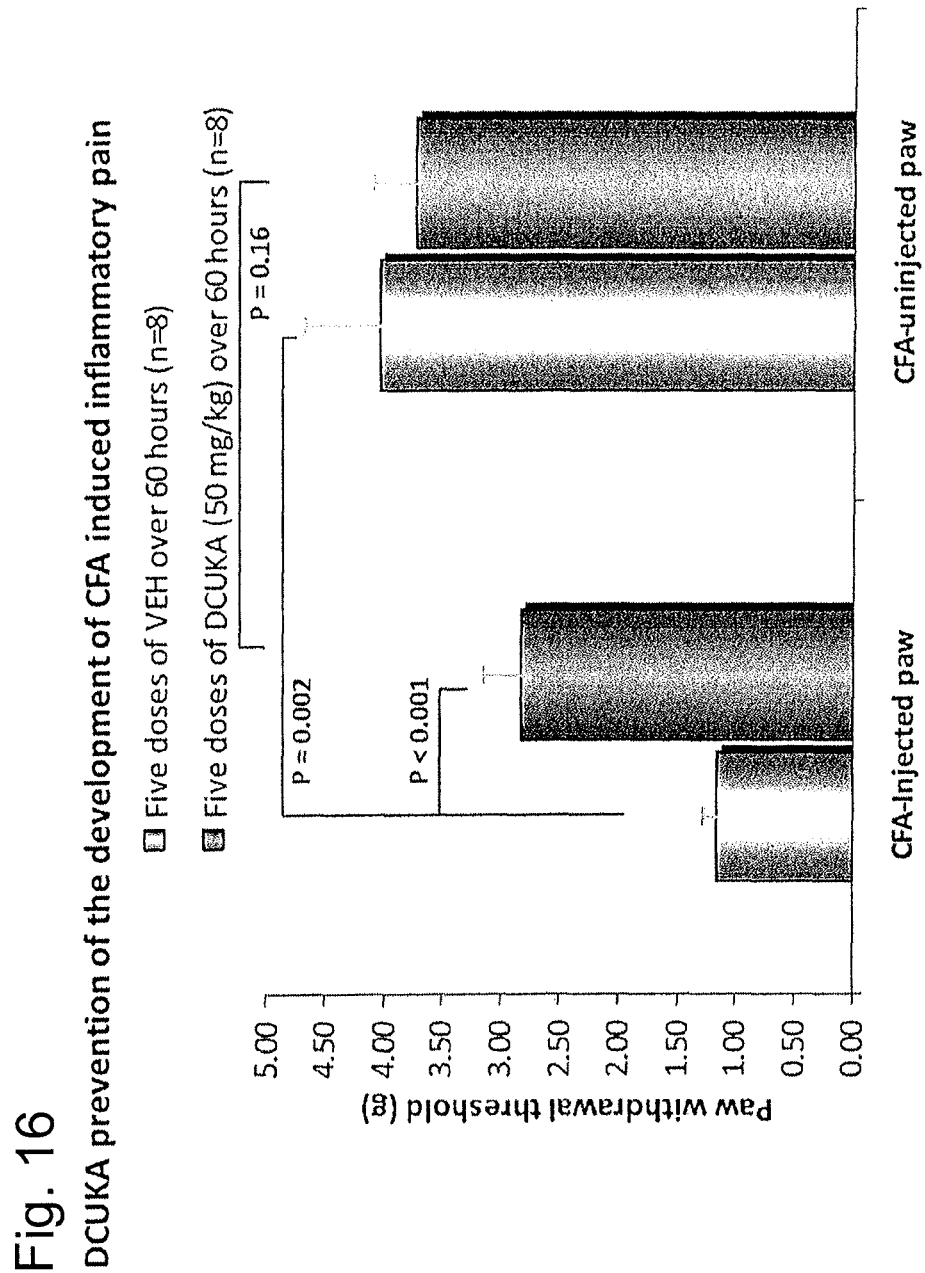
FIG. 16 illustrates graphically that administration of DCUKA following CFA injection prevents the development of CFA-induced neuropathic pain, measured by changes in the mechanical pain threshold.

FIG. 16 shows that DCUKA can prevent the development of neuropathic pain caused by CFA. Data show the ratio of the mechanical pain threshold at 60 hours after CFA treatment to the pre-CFA baseline mechanical pain threshold. CFA treatment significantly reduced the pain threshold by approximately 70%. However, when animals were given DCUKA daily prior to testing, the threshold was not reduced (P=0.16), and remained close to the baseline pain threshold, i.e., DCUKA has the ability to prevent the development of inflammatory pain, when given after administration of an inflammatory agent. Student's t-test is used to compare the pain threshold between group, and paired t-test is used to compare the pain threshold within group.

FIG. 17 illustrates that repeated DCUKA treatments during the period between the administration of cisplatin and pain testing, prevented the development of pain in the rat cisplatin-induced neuropathic pain model. Data are presented as mean±SEM of the mechanical pain threshold (paw withdrawal threshold). Injection of Cisplatin resulted in a significant decrease in mechanical pain threshold over days in the rats treated chronically with vehicle. With repeated DCUKA treatments, there was no statistically significant decrease of pain threshold compared to the pre-cisplatin baseline. The results show that DCUKA has the ability to prevent the development of chemotherapy-induced neuropathic pain, when given after the administration of the chemotherapeutic agent.

Two way repeated measure ANOVA revealed a statistically significant difference (P=0.023) between the two treatments, DCUKA and vehicle. The individual P values shown in the graph are for DCUKA versus vehicle and are calculated by the multiple comparison method. There are also significant differences detected in the pain threshold in the cisplatin and vehicle group (day 15, 19, 25, 32) compared to day 0, before cisplatin, but no significant differences in pain threshold between the cisplatin and DCUKA group compared to the Day 0 values prior to cisplatin injection).

Preferred embodiments of this invention have been described hereinabove, including the best mode known to the inventors for carrying out the invention. Variations of those preferred embodiments within the scope of this invention will become apparent to those of ordinary skill in the art upon reading the foregoing description. Accordingly, this invention includes all modifications and equivalents of the subject matter defined by the claims appended hereto. Moreover, any combination of the above-described elements in all possible variations thereof is encompassed by the invention unless otherwise indicated herein or otherwise clearly contradicted by context.

REFERENCES

Each document listed below is incorporated herein by reference in its entirety.

Baldini A, Von Korff M, Lin E H (2012) A Review of Potential Adverse Effects of Long-Term Opioid Therapy: A Practitioner's Guide. Prim Care Companion CNS Disord 14.

Barber J (2011) Examining the use of tramadol hydrochloride as an antidepressant. Exp Clin Psychopharmacol 19:123-130.

Basbaum A I, Bautista D M, Scherrer G, Julius D (2009) Cellular and molecular mechanisms of pain. Cell 139: 267-284.

Belkouch M, Dansereau M A, Tetreault P, Biet M, Beaudet N, Dumaine R, Chraibi A, Melik-Parsadaniantz S, Sarret P (2014) Functional up-regulation of Nav1.8 sodium channel in Abeta afferent fibers subjected to chronic peripheral inflammation. Journal of neuroinflammation 11:45.

Black J A, Liu S, Tanaka M, Cummins T R, Waxman S G (2004) Changes in the expression of tetrodotoxin-sensitive sodium channels within dorsal root ganglia neurons in inflammatory pain. Pain 108:237-247.

Bodnar R J (2000) Supraspinal circuitry mediating opioid antinociception: antagonist and synergy studies in multiple sites. J Biomed Sci 7:181-194.

Bozic I, Reiter J G, Allen B, Antal T, Chatterjee K, Shah P, Moon Y S, Yaqubie A, Kelly N, Le D T, Lipson E J, Chapman P B, Diaz L A, Jr., Vogelstein B, Nowak M A (2013) Evolutionary dynamics of cancer in response to targeted combination therapy. Elife 2:e00747.

Cao C. (2017) Flow Chemistry: pathway for continuous API manufacturing. Pharmaceutical Manufacturing, https://www.pharmasalmanac.com/articles/flow-chemistry-pathway-for-continuous-api-manufacturing.

Carvalho A F, Sharma M S, Brunoni A R, Vieta E, Fava G A (2016) The Safety, Tolerability and Risks Associated with the Use of Newer Generation Antidepressant Drugs: A Critical Review of the Literature. Psychother Psychosom 85:270-288.

Cashman J N (1996) The mechanism of action of NSAIDs in analgesia. Drugs 52 Suppl 5:13-23.

Childers W E, Jr., Baudy R B (2007) N-methyl-D-aspartate antagonists and neuropathic pain: the search for relief. J Med Chem 50:2557-2562.

Choi J S, Waxman S G (2011) Physiological interactions between Na(v)1.7 and Na(v)1.8 sodium channels: a computer simulation study. J Neurophysiol 106:3173-3184.

Chou R, Turner J A, Devine E B, Hansen R N, Sullivan S D, Blazina I, Dana T, Bougatsos C, Deyo R A (2015) The effectiveness and risks of long-term opioid therapy for chronic pain: a systematic review for a National Institutes of Health Pathways to Prevention Workshop. Ann Intern Med 162:276-286.

Chou T C (2010) Drug combination studies and their synergy quantification using the Chou-Talalay method. Cancer Res 70:440-446.

Coggeshall R E, Tate S, Carlton S M (2004) Differential expression of tetrodotoxin-resistant sodium channels Nav1.8 and Nav1.9 in normal and inflamed rats. Neurosci Lett 355:45-48.

Costigan M, Scholz J, Woolf C J (2009) Neuropathic pain: a maladaptive response of the nervous system to damage. Annu Rev Neurosci 32:1-32.

Davies S N, Lodge D (1987) Evidence for involvement of N-methylaspartate receptors in 'wind-up' of class 2 neurones in the dorsal horn of the rat. Brain Res 424:402-406.

Dib-Hajj S D, Cummins T R, Black J A, Waxman S G (2007) From genes to pain: Na v 1.7 and human pain disorders. Trends Neurosci 30:555-563.

Dickenson A H, Sullivan A F (1987) Evidence for a role of the NMDA receptor in the frequency dependent potentiation of deep rat dorsal horn nociceptive neurones following C fibre stimulation. Neuropharmacology 26:1235-1238.

Eijkelkamp N, Linley J E, Baker M D, Minett M S, Cregg R, Werdehausen R, Rugiero F, Wood J N (2012) Neurological perspectives on voltage-gated sodium channels. Brain 135:2585-2612.

Fava G A, Benasi G, Lucente M, Offidani E, Cosci F, Guidi J (2018) Withdrawal Symptoms after Serotonin-Noradrenaline Reuptake Inhibitor Discontinuation: Systematic Review. Psychother Psychosom 87:195-203.

Fernandez-Montoya J, Avendano C, Negredo P (2017) The Glutamatergic System in Primary Somatosensory Neurons and Its Involvement in Sensory Input-Dependent Plasticity. Int J Mol Sci 19.

Ferrari L F, Lotufo C M, Araldi D, Rodrigues M A, Macedo L P, Ferreira S H, Parada C A (2014) Inflammatory sensitization of nociceptors depends on activation of NMDA receptors in DRG satellite cells. Proc Natl Acad Sci USA 111:18363-18368.

Foucquier J, Guedj M (2015) Analysis of drug combinations: current methodological landscape. Pharmacol Res Perspect 3:e00149.

Galizzi J P, Lockhart B P, Bril A (2013) Applying systems biology in drug discovery and development. Drug Metabol Drug Interact 28:67-78.

Gaunitz C, Schuttler A, Gillen C, Allgaier C (2002) Formalin-induced changes of NMDA receptor subunit expression in the spinal cord of the rat. Amino Acids 23:177-182.

Institute of Medicine (2011), Relieving pain in America: A Blueprint for Transforming Prevention, Care, Education and Research, National Academics Press, Washington, D.C.

Iwata H, Takasusuki T, Yamaguchi S, Hori Y (2007) NMDA receptor 2B subunit-mediated synaptic transmission in the superficial dorsal horn of peripheral nerve-injured neuropathic mice. Brain Res 1135:92-101.

Jang J H, Kim D W, Sang Nam T, Se Paik K, Leem J W (2004) Peripheral glutamate receptors contribute to mechanical hyperalgesia in a neuropathic pain model of the rat. Neuroscience 128:169-176.

Karlsson U, Sjodin J, Angeby Moller K, Johansson S, Wikstrom L, Nasstrom J (2002) Glutamate-induced currents reveal three functionally distinct NMDA receptor populations in rat dorsal horn—effects of peripheral nerve lesion and inflammation. Neuroscience 112:861-868.

Kirkpatrick D R, McEntire D M, Smith T A, Dueck N P, Kerfeld M J, Hambsch Z J, Nelson T J, Reisbig M D, Agrawal D K (2016) Transmission pathways and mediators as the basis for clinical pharmacology of pain. Expert Rev Clin Pharmacol:1-25.

Laedermann C J, Abriel H, Decosterd I (2015) Post-translational modifications of voltage-gated sodium channels in chronic pain syndromes. Front Pharmacol 6:263.

Lai J, Porreca F, Hunter J C, Gold M S (2004) Voltage-gated sodium channels and hyperalgesia. Annu Rev Pharmacol Toxicol 44:371-397.

Lawrence J (2012) Nav1.7: a new channel for pain treatment. Pharmaceutical Journal.

Leung E L, Cao Z W, Jiang Z H, Zhou H, Liu L (2013) Network-based drug discovery by integrating systems biology and computational technologies. Brief Bioinform 14:491-505.

Li P, Huang C, Fu Y, Wang J, Wu Z, Ru J, Zheng C, Guo Z, Chen X, Zhou W, Zhang W, Li Y, Chen J, Lu A, Wang Y (2015) Large-scale exploration and analysis of drug combinations. Bioinformatics 31:2007-2016.

Liu Y, Hu B, Fu C, Chen X (2010) DCDB: drug combination database. Bioinformatics 26:587-588.

Loewe S M H (1926) uber Kombinations swirkungen. Arch für Exp Pathol 114:313-326.

Lozada C J and Diamond H S (2008) Osteoarthritis medication: Analgesics, other, nonsteroidal anti-inflammatory. Medscape.

Lunn M P, Hughes R A, Wiffen P J (2014) Duloxetine for treating painful neuropathy, chronic pain or fibromyalgia. Cochrane Database Syst Rev:CD007115.

Marcum Z A, Hanlon J T (2010) Recognizing the Risks of Chronic Nonsteroidal Anti-Inflammatory Drug Use in Older Adults. Ann Longterm Care 18:24-27.

Millan M J (2014) On 'polypharmacy' and multi-target agents, complementary strategies for improving the treatment of depression: a comparative appraisal. Int J Neuropsychopharmacol 17:1009-1037.

Minami K, Ogata J, Uezono Y (2015) What is the main mechanism of tramadol? Naunyn Schmiedebergs Arch Pharmacol 388:999-1007.

Moore R A, Wiffen P J, Derry S, Toelle T, Rice A S (2014) Gabapentin for chronic neuropathic pain and fibromyalgia in adults. Cochrane Database Syst Rev:CD007938.

Petrenko A B, Yamakura T, Baba H, Shimoji K (2003) The role of N-methyl-D-aspartate (NMDA) receptors in pain: a review. Anesth Analg 97:1108-1116.

Ramsay R R, Popovic-Nikolic M R, Nikolic K, Uliassi E, Bolognesi M L (2018) A perspective on multi-target drug discovery and design for complex diseases. Clin Transl Med 7:3.

Reuben D B, Alvanzo A A, Ashikaga T, Bogat G A, Callahan C M, Ruffing V, Steffens D C (2015) National Institutes of Health Pathways to Prevention Workshop: the role of opioids in the treatment of chronic pain. Ann Intern Med 162:295-300.

Rozanski G M, Li Q, Stanley E F (2013) Transglial transmission at the dorsal root ganglion sandwich synapse: glial cell to postsynaptic neuron communication. Eur J Neurosci 37:1221-1228.

Schneider C, Yale, S H and Larson M (2003) Principles of pain management. *Clinical Medicine & Research* 1:337-340

Schreiber A K, Nones C F, Reis R C, Chichorro J G, Cunha J M (2015) Diabetic neuropathic pain: Physiopathology and treatment. World J Diabetes 6:432-444.

Smith H S, Smith E J, Smith B R (2012) Duloxetine in the management of chronic musculoskeletal pain. Ther Clin Risk Manag 8:267-277.

Sofat N, Harrison A, Russell M D, Ayis S, Kiely P D, Baker E H, Barrick T R, Howe F A (2017) The effect of pregabalin or duloxetine on arthritis pain: a clinical and mechanistic study in people with hand osteoarthritis. J Pain Res 10:2437-2449.

Tabakoff B, Ren W, Vanderlinden L, Snell L D, Matheson C J, Wang Z J, Levinson R, Smothers C T, Woodward J J, Honse Y, Lovinger D, Rush A M, Sather W A, Gustafson D L, Hoffman P L (2016) A novel substituted aminoquinoline selectively targets voltage-sensitive sodium channel isoforms and NMDA receptor subtypes and alleviates chronic inflammatory and neuropathic pain. Eur J Pharmacol 784:1-14.

Talevi A (2015) Multi-target pharmacology: possibilities and limitations of the "skeleton key approach" from a medicinal chemist perspective. Front Pharmacol 6:205.

Tallarida R J (2001) Drug synergism: its detection and applications. J Pharmacol Exp Ther 298:865-872.

Taneja A, Della Pasqua O, Danhof M (2017) Challenges in translational drug research in neuropathic and inflammatory pain: the prerequisites for a new paradigm. Eur J Clin Pharmacol 73:1219-1236.

Theile J W, Cummins T R (2011) Recent developments regarding voltage-gated sodium channel blockers for the treatment of inherited and acquired neuropathic pain syndromes. Front Pharmacol 2:54.

Volkow N D, McLellan A T (2016) Opioid Abuse in Chronic Pain—Misconceptions and Mitigation Strategies. N Engl J Med 374:1253-1263.

Wang W, Gu J, Li Y Q, Tao Y X (2011) Are voltage-gated sodium channels on the dorsal root ganglion involved in the development of neuropathic pain? Mol Pain 7:16.

Wempe M F, Lightner J W, Miller B, Iwen T J, Rice P J, Wakui S, Anzai N, Jutabha P, Endou H (2012) Potent human uric acid transporter 1 inhibitors: in vitro and in vivo metabolism and pharmacokinetic studies. Drug Des Devel Ther 6:323-339.

Wilson J A, Garry E M, Anderson H A, Rosie R, Colvin L A, Mitchell R, Fleetwood-Walker S M (2005) NMDA receptor antagonist treatment at the time of nerve injury prevents injury-induced changes in spinal NR1 and NR2B subunit expression and increases the sensitivity of residual pain behaviours to subsequently administered NMDA receptor antagonists. Pain 117:421-432.

Wood J N, Boorman J P, Okuse K, Baker M D (2004) Voltage-gated sodium channels and pain pathways. J Neurobiol 61:55-71.

Worley S L (2016) New Directions in the Treatment of Chronic Pain: National Pain Strategy Will Guide Prevention, Management, and Research. P T 41:107-114.

Yekkirala A S, Roberson D P, Bean B P, Woolf C J (2017) Breaking barriers to novel analgesic drug development. Nat Rev Drug Discov 16:810.

Zimmermann G R, Lehar J, Keith C T (2007) Multi-target therapeutics: when the whole is greater than the sum of the parts. Drug Discov Today 12:34-42.

The invention claimed is:

1. A pharmaceutical composition comprising an aminoquinoline compound of Formula

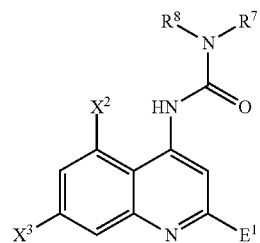

in free acid form, free base form, or as a pharmacologically acceptable addition salt wherein:
   $R^7$ is alkyl (preferably a 3 to 6 carbon alky), or phenyl;
   $R^8$ is alkyl (preferably a 3 to 6 carbon alkyl), or phenyl;
   $E^1$ is —C(=O)$R^9$;
   each $R^9$ is H or $C_1$-$C_4$ alkyl;
   each $X^2$ and $X^3$ independently is an electron withdrawing group (preferably halogen or nitro);
together with an analgesic agent different from the aminoquinoline compound and selected from the group consisting of a NSAID, an opioid, a NE/5-HT reuptake inhibitor, and mixtures thereof.

2. The composition of claim 1 wherein the aminoquinoline compound is 5,7-dichloro-4-(3,3-dibutylureido) quinolone-2-carboxylic acid (BCUKA).

3. The composition of claim 1 wherein the aminoquinoline compound is 5,7-dichloro-4-(3,3-diphenylureido) quinolone-2-carboxylic acid (DCUKA).

4. The composition of claim 1 wherein the aminoquinoline compound is 5,7-dichloro-4-(3,3-diphenylureido) quinolone-2-carboxyethyl ester DCUK-OEt).

5. The composition of claim 1 wherein the analgesic agent is a non-steroidal anti-inflammatory drug (NSAID).

6. The composition of claim 5 wherein the analgesic agent is aspirin.

7. The composition of claim 5 wherein the analgesic agent is diclofenac.

8. The composition of claim 1 wherein the analgesic agent is an opiate.

9. The composition of claim 8 wherein the analgesic agent is morphine.

10. The composition of claim 8 wherein the analgesic agent is oxycodone.

11. The composition of claim 8 wherein the analgesic agent is methadone.

12. The composition of claim 1 wherein the analgesic agent is tramadol.

13. A method of treating chronic pain comprising administering to a subject suffering from chronic pain the composition of claim 1.

14. The method of claim 13 wherein the aminoquinoline compound is 5,7-dichloro-4-(3,3-dibutylureido) quinolone-2-carboxylic acid (BCUKA).

15. The method of claim 13 wherein the analgesic agent is morphine.

16. The method of claim 13 wherein the analgesic agent is oxycodone.

17. The method of claim 13 wherein the analgesic agent is methadone.

18. The method of claim 13 wherein the analgesic agent is tramadol.

19. The method of claim 13 wherein the analgesic agent is aspirin.

20. The method of claim 13 wherein the analgesic agent is diclofenac.

21. The method of claim 13 wherein the aminoquinoline compound is 5,7-dichloro-4-(3,3-diphenylureido) quinolone-2-carboxylic acid (DCUKA).

22. The method of claim 21 wherein the analgesic agent is morphine.

23. The method of claim 21 wherein the analgesic agent is oxycodone.

24. The method of claim 21 wherein the analgesic agent is methadone.

25. The method of claim 21 wherein the analgesic agent is tramadol.

26. The method of claim 21 wherein the analgesic agent is aspirin.

27. The method of claim 21 wherein the analgesic agent is diclofenac.

28. The method of claim 13 wherein the aminoquinoline compound is 5,7-dichloro-4-(3,3-diphenylureido) quinolone-2-carboxylethyl ester (DCUK-OEt).

29. The method of claim 28 wherein the analgesic agent is morphine.

30. The method of claim 28 wherein the analgesic agent is oxycodone.

31. The method of claim 28 wherein the analgesic agent is methadone.

32. The method of claim 28 wherein the analgesic agent is tramadol.

33. The method of claim 28 wherein the analgesic agent is aspirin.

34. The method of claim 28 wherein the analgesic agent is diclofenac.

35. A method of potentiating the effect of an analgesic compound in a patient suffering from chronic pain comprising administering to the patient an effective amount of the composition of claim 1.

36. The method of claim 35 wherein the analgesic agent is at least one compound selected from the group consisting of an opiate and an NSAID and a NE/5-HT reuptake inhibitor.

37. The method of claim 36 wherein the opiate is morphine.

38. The method of claim 36 wherein the opiate is oxycodone.

39. The method of claim 36 wherein the opiate is methadone.

40. The method of claim 36 wherein the NE/5-HT reuptake inhibitor is tramadol.

41. The method of claim 36 wherein the NSAID is aspirin.

42. The method of claim 36 wherein the NSAID is diclofenac.

43. The method of claim 35 wherein the aminoquinoline compound is 5,7-dichloro-4-(3,3-dibutylureido) quinolone-2-carboxylic acid (BCUKA).

44. The method of claim 35 wherein the aminoquinoline compound is 5,7-dichloro-4-(3,3-diphenylureido) quinolone-2-carboxylic acid (DCUKA).

45. The method of claim 35 wherein the aminoquinoline compound is 5,7-dichloro-4-(3,3-diphenylureido) quinolone-2-carboxylethyl ester (DCUK-OEt).

46. A method for treating chronic pain in an individual after the individual has sustained an injury, chemically-induced nerve damage and/or pathologically-induced nerve damage which comprises administering to the individual an effective amount of the composition of claim 1.

* * * * *